United States Patent
Schepis et al.

(10) Patent No.: US 11,504,534 B2
(45) Date of Patent: Nov. 22, 2022

(54) DEVICE AND METHOD TO SELECTIVELY AND REVERSIBLY MODULATE A NERVOUS SYSTEM STRUCTURE TO INHIBIT THE PERCEPTION OF PAIN

(71) Applicant: Avent, Inc., Alpharetta, GA (US)

(72) Inventors: Eric A. Schepis, Alpharetta, GA (US); David M. Page, Alpharetta, GA (US); Natalia Alexeeva, Alpharetta, GA (US); Lee C. Burnes, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 16/705,904

(22) Filed: Dec. 6, 2019

(65) Prior Publication Data

US 2020/0179698 A1 Jun. 11, 2020

Related U.S. Application Data

(60) Provisional application No. 62/776,908, filed on Dec. 7, 2018, provisional application No. 62/776,926, filed on Dec. 7, 2018.

(51) Int. Cl.
*A61N 1/36* (2006.01)
*A61N 1/05* (2006.01)

(52) U.S. Cl.
CPC ....... *A61N 1/36075* (2013.01); *A61N 1/0509* (2013.01); *A61N 1/0512* (2013.01); *A61N 1/0521* (2013.01); *A61N 1/0546* (2013.01); *A61N 1/3614* (2017.08); *A61N 1/36139* (2013.01); *A61N 1/36142* (2013.01); *A61N 1/36171* (2013.01); *A61N 1/36175* (2013.01)

(58) Field of Classification Search
None
See application file for complete search history.

(56) References Cited

U.S. PATENT DOCUMENTS

| 9,220,895 B2 * | 12/2015 | Siff ................... A61N 1/36021 |
| 11,253,312 B2 * | 2/2022 | Fox ................... A61B 18/1492 |
| 2004/0167583 A1 * | 8/2004 | Knudson ................. A61N 1/05 607/40 |

(Continued)

FOREIGN PATENT DOCUMENTS

| GB | 2571919 A | 9/2019 |
| WO | 2001097905 A1 | 12/2001 |

(Continued)

OTHER PUBLICATIONS

Examination Report, dated Jun. 30, 2022, received in connection with corresponding GB Patent Application No. 1917902.7.

*Primary Examiner* — Carl H Layno
*Assistant Examiner* — Manolis Pahakis
(74) *Attorney, Agent, or Firm* — Meunier Carlin & Curfman LLC

(57) ABSTRACT

The present disclosure is directed to a system and method for selectively and reversibly modulating targeted neural and non-neural tissue of a nervous system for the treatment of pain. An electrical stimulation is delivered to the treatment site that selectively and reversibly modulates the targeted neural- and non-neural tissue of the nervous structure, inhibiting the perception of pain while preserving other sensory and motor function, and proprioception.

18 Claims, 14 Drawing Sheets

(56) References Cited

U.S. PATENT DOCUMENTS

| | | | | |
|---|---|---|---|---|
| 2004/0220644 | A1* | 11/2004 | Shalev | A61N 1/36082 607/45 |
| 2005/0038484 | A1* | 2/2005 | Knudson | A61N 1/36007 607/58 |
| 2007/0083245 | A1* | 4/2007 | Lamensdorf | A61N 1/36082 607/45 |
| 2008/0172102 | A1* | 7/2008 | Shalev | A61N 1/0548 607/45 |
| 2011/0098777 | A1* | 4/2011 | Silverstone | A61N 1/36025 607/45 |
| 2012/0071811 | A1* | 3/2012 | Ansarinia | A61N 1/36075 604/20 |
| 2013/0253613 | A1* | 9/2013 | Salahovic | A61N 1/36021 607/61 |
| 2014/0214120 | A1* | 7/2014 | Simon | A61N 1/3787 607/46 |
| 2015/0174406 | A1* | 6/2015 | Lamensdorf | A61N 1/36057 607/62 |
| 2016/0030408 | A1* | 2/2016 | Levin | A61K 31/573 514/330 |
| 2016/0038741 | A1* | 2/2016 | Perryman | A61N 1/36071 607/46 |
| 2018/0056066 | A1* | 3/2018 | Boggs | A61N 1/36071 |
| 2018/0133460 | A1* | 5/2018 | Townley | A61B 18/1492 |
| 2019/0201694 | A1* | 7/2019 | Hsu | A61N 1/36075 |
| 2019/0201695 | A1* | 7/2019 | Hsu | A61N 1/37241 |
| 2020/0179690 | A1* | 6/2020 | Schepis | A61N 1/36135 |
| 2020/0179698 | A1* | 6/2020 | Schepis | A61N 1/3614 |
| 2020/0269046 | A1* | 8/2020 | Page | A61N 1/16 |
| 2021/0022948 | A1* | 1/2021 | Musallam | A61K 9/0048 |

FOREIGN PATENT DOCUMENTS

| | | |
|---|---|---|
| WO | 2011109080 A2 | 9/2011 |
| WO | 2017142948 A1 | 8/2017 |

\* cited by examiner

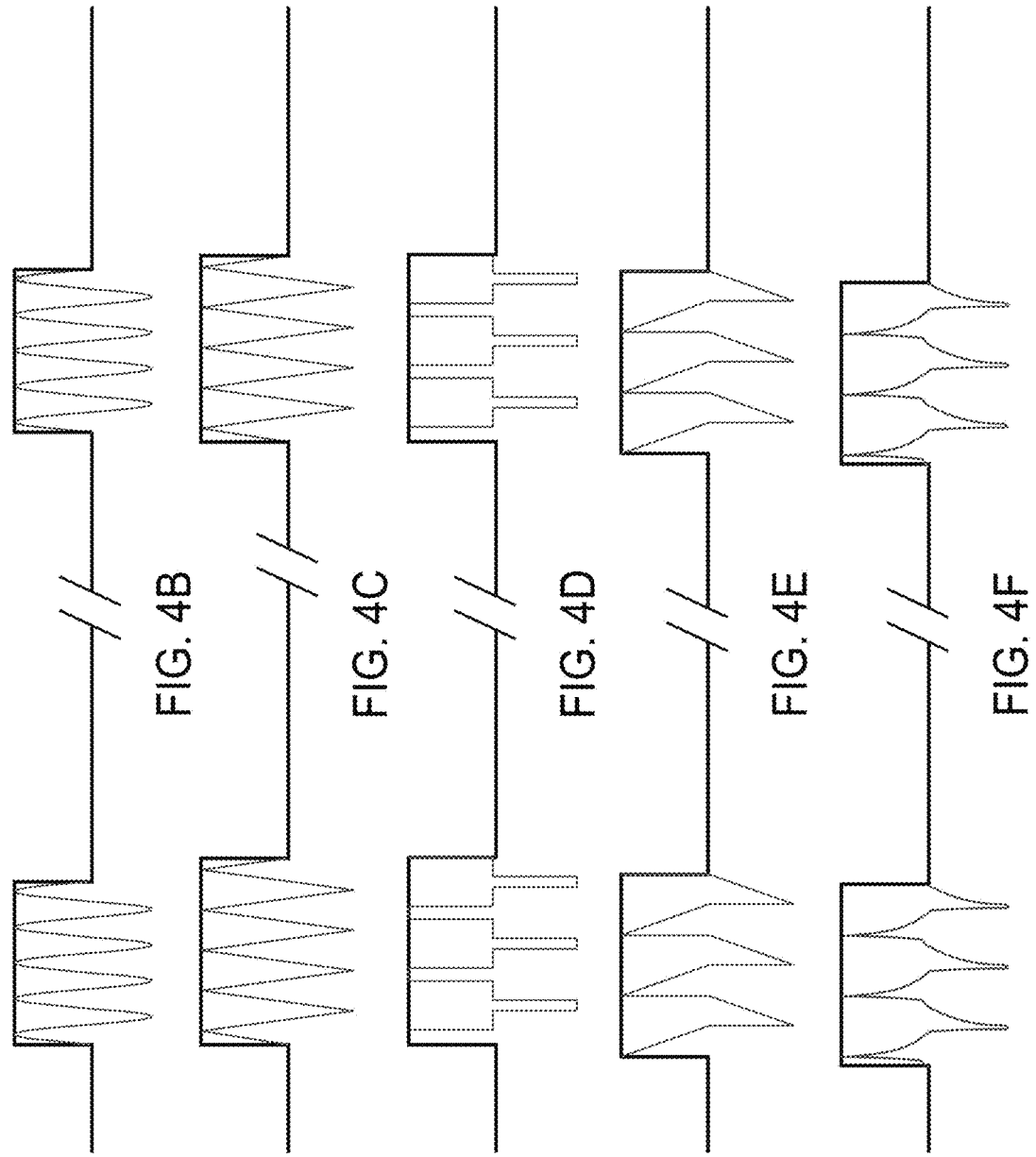

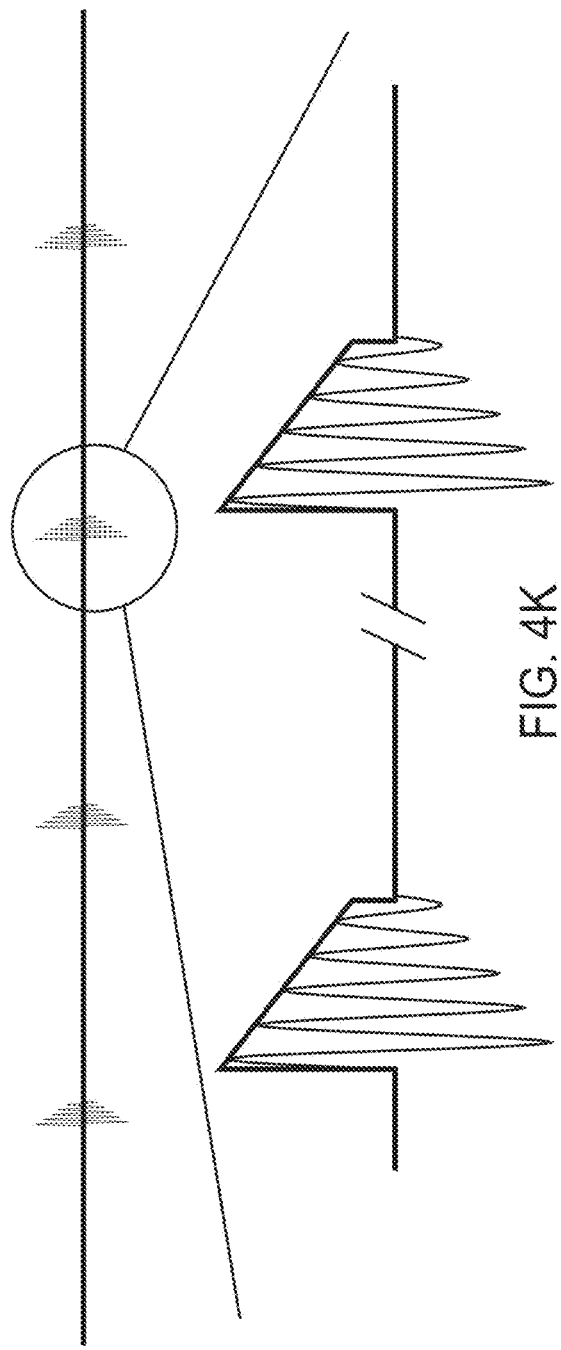
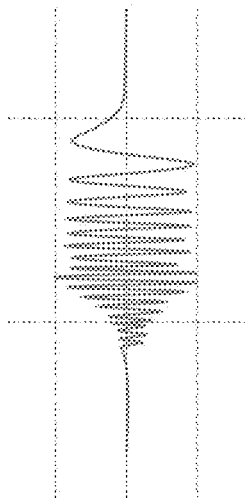
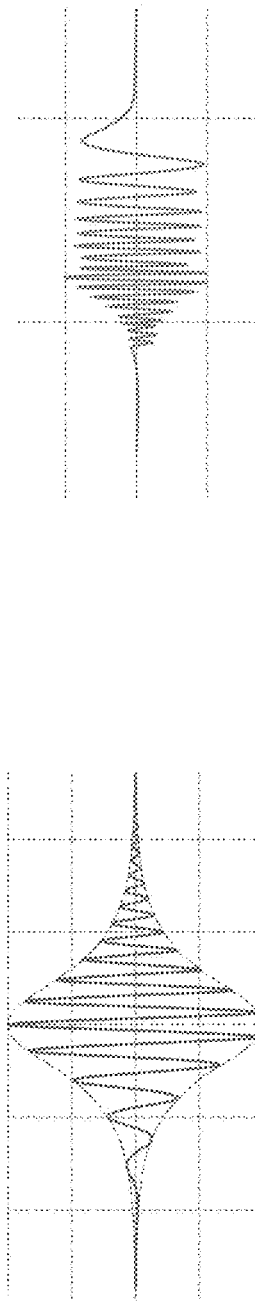

DEVICE AND METHOD TO SELECTIVELY AND REVERSIBLY MODULATE A NERVOUS SYSTEM STRUCTURE TO INHIBIT THE PERCEPTION OF PAIN

CROSS-REFERENCE TO RELATED APPLICATIONS

This application claims priority to U.S. Provisional Application Nos. 62/776,926 and 62/776,908, both of which were filed on Dec. 7, 2018, and are incorporated herein by reference in their entirety.

TECHNICAL FIELD

The present invention relates generally to a device and method to modulate neural and non-neural tissue activity to treat pain. In particular, a device and method to selectively and reversibly modulate neural- and non-neural tissue of a nervous structure to inhibit the perception of pain while preserving other sensory and motor function, and proprioception.

BACKGROUND OF THE INVENTION

Pain can be treated by both destructive and non-destructive methods by disrupting the transmission of pain signals that originate in the body from reaching the brain. Destructive methods are routinely used to treat chronic pain indications, and include thermal ablation, cryoablation, chemical ablations (e.g., via phenols, lidocaine, Botox™, ultrasonography ablation and mechanical transection). However, destruction of the nervous structure causes an immediate loss of functionality in the nerve and may lead to long-term atrophy, neuropathy and ultimately more pain. Additionally, mixed nerves and ganglia are typically not targeted using destructive interventions for chronic pain because of the desire to maintain motor and non-painful sensory function. Further, destruction of a nervous structure is not conducive to post-operative and peri-operative pain management, where motor and non-painful sensory function is desired to be preserved. Consequently, destructive methods for disrupting pain signals are generally not used for acute pain applications such as post-surgical pain.

Non-destructive methods to treat pain include the use of prescription pain medications (e.g., opioids), local anesthetic injections, topical or injected cocktails consisting of steroids and other anti-inflammatory agents, continuous infusion of local anesthetics, electrical blocking, electrical stimulation, and the application of pulsed radiofrequency energy. Each of these methods have a unique set of challenges that compromise treatment efficacy and usability. For instance, prescription pain medications come with unwanted side effects and can lead to addiction. Meanwhile, local anesthetic and cocktail injections have a short effective duration that only lasts for a few hours, while continuous infusion of anesthetics requires an external device be tethered to the patient for long-term treatment (days). Additionally, the use of local anesthetics presents a risk of nerve toxicity, vascular toxicity and allergic reactions. Lastly, these agents are not selective to the type of nerve activity that they block (e.g., they block both nerve fiber activity associated with pain and nerve fiber activity associated with motor function).

Electrical neuromodulation techniques pose a lower risk of side-effects than chemical interventions and provide adjustable, regional management of pain. However, existing electrical blocking technologies are only being used to treat chronic post-amputation pain and require an internal pulse generator and nerve cuff be implanted in the patient for long-term blocking. As such, the need for surgical implantation considerably burdens the use of electrical blocking for acute pain applications in both small and large nerves, as well electrical blocking of acute head and face pain. Moreover, even though electrical stimulation devices are commonly used to mitigate pain, their efficacy thus far has not been sufficient to manage moderate to severe pain levels, such as the pain levels experienced by a patient suffering from severe or chronic migraine, peri-operative pain and/or post-operative pain experience in the days to weeks following surgery. Electrical nerve stimulation devices have also been used in peripheral nerves, on the dorsal root ganglia, and in the spinal cord to treat chronic pain, however, these devices are all burdened by the need for surgical implantation and may undesirably activate motor fibers or non-painful sensory fibers when applied to mixed nerves or ganglia. Further, although radiofrequency energy treatment is procedural-based, and the patient is not burdened by a take-home device, it cannot be used to treat large nerves, and the treatment outcomes are inconsistent for small nerves. Additionally, the selectivity and time-course of reversibility of radiofrequency energy treatment for acute pain is unknown.

As such, there is a need for an electrical device and method that can temporarily and selectively inhibit perception of pain by modulating neural and non-neural activity in both small-diameter and large-diameter peripheral nerves, cranial nerves, ganglia, autonomic nerves, plexuses and the spinal cord, with effects that last for days-to-weeks, where the temporary and selective blocking does not run the risk of neural toxicity, vascular toxicity or allergy.

SUMMARY OF THE INVENTION

The present disclosure is directed to a system and method for selectively and reversibly modulating targeted neural and non-neural tissue of a nervous system for the treatment of pain. An electrical stimulation is delivered to the treatment site that selectively and/or reversibly modulates the targeted neural- and non-neural tissue of the nervous structure, inhibiting the perception of pain while preserving other sensory and motor function, and proprioception. In an aspect, a system is disclosed for selectively and/or reversibly modulating targeted neural- and non-neural tissue of a nervous system structure (e.g., to treat a medical condition of a patient). The system includes an electrical stimulation device comprising an electrode sized and configured to be placed adjacent (e.g., near, contacting) a mucosal tissue of the patient (e.g., having a size-, shape-, and contact-surface configuration suitable to deliver an electrical stimulation to the targeted nervous system structure and adjacent non-neural tissue) (e.g., monopolar or bipolar) (e.g., a single electrode or an array of electrodes), the electrode delivering an electrical stimulation to a treatment site proximate the targeted neural- and non-neural tissue of the nervous system structure underlying the mucosal tissue; a controller configured to connect to the electrode of the electrical stimulation device and to a power source configured to supply electrical energy to the electrode, where the controller is configured to direct operation of the electrical stimulation device (e.g., via current controlled, voltage controlled, power controlled, and/or temperature controlled) to apply the electrical stimulation to the treatment site through the electrode, wherein the application of the electrical stimulation to the treatment site selectively modulates the targeted neural- and non-neural tissue of the nervous system structure inhibiting the perception of pain and preserving other sensory and motor function, and proprioception, and wherein the application of the electrical stimulation to the treatment site does not damage the mucosal tissue.

In some embodiments, the controller directs operation of the electrical stimulation device to administer a single application of the electrical stimulation to the treatment site to selectively modulate the targeted neural- and non-neural tissue and to result in subsequent inhibition of perception of pain, for a period of about 1 day to about 30 days.

In some embodiments, the pain comprises at least one of head-and-face pain, a migraine headache, a cluster headache, an occipital neuralgia, a tension headache, a sinus headache, cervicogenic headache, postherpetic neuralgia, post-traumatic pain, chronic daily headache (transformed migraine).

In some embodiments, the mucosal tissue comprises at least one of an oral mucosa, a nasal oral mucosa, a gastrointestinal (GI) tract mucosa, a bowel mucosa, a bladder mucosa, and where the electrode is sized and configured to be placed adjacent the mucosal tissue.

In some embodiments, the nervous structure comprises at least one of a sphenopalatine ganglion and a gasserian ganglion, and where the electrode is configured to deliver electrical stimulation to the treatment site proximate the targeted neural- and non-neural tissue of the nervous structure.

In some embodiments, the controller is configured to direct operation of the electrical stimulation device to apply electrical stimulation to the treatment site to modulate the targeted neural- and non-neural tissue thereby inhibiting nerve signal transmission through nerve fibers that are responsible for the transmission of pain (e.g., and transmission of thermoception, autonomic effector activity and/or visceral function), while nerve signal transmission through nerve fibers responsible for other sensory and motor function, and proprioception is preserved, wherein other sensory function includes at least one of touch, vision, audition, gustation, olfaction, and balance.

In some embodiments, the controller is adjustable to vary a parameter of the electrical stimulation delivered to the treatment site to modulate the targeted neural and non-neural tissue and modulate nerve signal transmission through nerve fibers of the nervous system structure responsible for the transmission of pain, wherein the parameter is selected from the group consisting of a waveform shape, a waveform frequency, a waveform amplitude, an electrical field strength generated at the electrode (e.g., as measured at the electrode or at the treatment site), a waveform DC offset, and a waveform duty cycle, a tissue temperature, an electrode temperature, a cooling mechanism parameter (e.g., a rate of cooling, flow rate of cooling medium, cooling medium pressure, measured temperature at treatment site, a portion of cooling mechanism, and/or a portion of the electrode), and a treatment duration.

In some embodiments, the electrical stimulation selectively inhibits nerve signal transmission through at least one of a select type of nerve fiber of the nervous system structure (e.g., parasympathetic nerve fibers, sympathetic nerve fibers, sensory nerve fibers), wherein function of at least one of a non-selected nerve fiber (e.g., parasympathetic nerve fibers, sympathetic nerve fibers, and sensory nerve fibers) is selectively preserved.

In some embodiments, electrical stimulation delivered to the target site differentially inhibits the function of the select type of nerve fiber, wherein the select type of nerve fiber has a larger percentage of fibers inhibited than the non-selected type of nerve fiber of the nervous system structure (e.g., parasympathetic nerve fibers, sympathetic nerve fibers, sensory nerve fibers) and the non-neural tissue.

In some embodiments, the nervous system structure comprises the sphenopalatine ganglion (SPG) and the electrode is sized and configured to be positioned adjacent the mucosal tissue adjacent the SPG (e.g., having a size-, shape-, and contact-surface configuration suitable to deliver the electrical stimulation to the SPG and adjacent non-neural tissue), wherein the electrical stimulation selectively inhibits nerve signal transmission through at least one of a select type of nerve fiber of the SPG (e.g., the parasympathetic nerve fibers comprising the SPG, the sympathetic nerve fibers comprising the SPG, and the sensory nerve fibers comprising the SPG), wherein function of at least one of a non-selected nerve fiber (e.g., parasympathetic nerve fibers comprising the SPG, sympathetic nerve fibers comprising the SPG, and sensory nerve fibers comprising the SPG) is selectively preserved.

In some embodiments, the electrical stimulation delivered to the target site differentially inhibits the function of the select type of nerve fiber of the SPG, wherein the select type of nerve fiber of the SPG has a larger percentage of fibers inhibited than the non-selected type of fiber of the SPG (e.g., parasympathetic nerve fibers, sympathetic nerve fibers, sensory nerve fibers) and the non-neural tissue.

In some embodiments, wherein the nervous system structure comprises the sphenopalatine ganglion (SPG), the controller is adjustable to vary a parameter of the electrical stimulation delivered to the treatment site to selectively modulate the neural and non-neural tissue of the SPG and selectively modulate nerve signal transmission through nerve fibers of the SPG responsible for the transmission of pain, wherein the parameter is selected from the group consisting of a waveform shape, a waveform frequency, a waveform amplitude, an electrical field strength generated at the electrode (e.g., as measured at the electrode or at the treatment site), a waveform DC offset, and a waveform duty cycle, a tissue temperature, an electrode temperature, a cooling mechanism parameter (e.g., a rate of cooling, flow rate of cooling medium, cooling medium pressure, measured temperature at treatment site, a portion of cooling mechanism, and/or a portion of the electrode), and a treatment duration.

In some embodiments, the electrical stimulation delivered to the target site for modulating function of the SPG (e.g., nerve signal transmission through parasympathetic nerve fibers of the SPG) has a frequency range of about 100 kHz to about 1 MHz, intensity ≤1,000 mA and ≤1,000 V (peak-to-peak), and an electrical field strength ≤1,000,000 V/m.

In some embodiments, the waveform of the electrical stimulation is pulsed with an envelope ≤1000 ms, an envelope delivery frequency ≤100 Hz, and for durations ≤30 minutes.

In some embodiments, the controller is adjustable to deliver electrical stimulation to the treatment site having a frequency selected from the group consisting of about 100 kHz, about 200 kHz, about 300 kHz, about 400 kHz, about 500 kHz, about 600 kHz, about 700 kHz, about 800 kHz, about 900 kHz and about 1 MHz.

In some embodiments, the electrical stimulation delivered to the target site has an amplitude range between about 10 mA and about 5,000 mA (peak-to-peak).

In some embodiments, the electrical stimulation delivered to the target site has an amplitude range between about 10 V and about 1,000 V (peak-to-peak).

In some embodiments, the electrical stimulation delivered to the treatment site has a power range between about 1 W and about 1,250 W.

In some embodiments, the electrical stimulation delivered to the treatment site generates or induces an electrical field strength at the target site and/or the electrode between about 20 V/m and about 1,000,000 V/m.

In some embodiments, the electrical stimulation delivered to the treatment site has a waveform shape component (e.g., a continuously outputted waveform or an intermittently outputted waveform (e.g., pulsed for a predefined duration)) (e.g., as a charge-balanced waveform or as a non-charge-balanced waveform) including at least one of a sinusoidal waveform, a square waveform, a triangular waveform, an impulse waveform, a shape modulated waveform, a frequency modulated waveform, an amplitude modulated waveform that provides a continuous delivery of electrical stimulation (e.g., a chirp) at the treatment site and a combination (e.g., additive combination) thereof.

In some embodiments, the electrical stimulation delivered to the treatment site has a duty cycle between about 0.1% and about 99%.

In some embodiments, the electrical stimulation delivered to the treatment site has an inter-pulse width between about 1 ms and about 999 ms.

In some embodiments, the electrical stimulation is delivered to the treatment site for a duration up to 30 minutes.

In some embodiments, the controller is adjustable to apply the electrical stimulation while maintaining the tissue temperature and/or electrode temperature between about 5° C. and about 60° C.

In some embodiments, the controller comprises a stimulator (e.g., a function or waveform generator) (e.g., an external function or waveform generator), the stimulator being coupled to both the electrode and an interface of the controller, where operation of the stimulator is directed by the controller to provide the electrical stimulation to the electrode.

In some embodiments, the electrode comprises at least two electrical contacts (e.g., wherein the at least two electrical contacts are configured to be positioned near the nervous system structured during treatment (e.g., where the electrical contacts are positioned at a distal end of the stimulation device)), wherein the controller is configured to independently (e.g., in a multipolar manner to direct current of the resultant electric filed) each of the at least to electrical contacts.

In some embodiments, the electrode is a monopolar electrode configured to be positioned at a contact surface of the stimulation device, and a return electrode is positioned on an outer surface of the patient's skin.

In some embodiments, the electrode is sized (e.g., contact an electrical contact of the electrode has a surface area ranging from about 1 mm$^2$ to about 100 mm$^2$) and/or shaped (e.g., elongated triangular shape, a ball-tipped, or half-ball, or flat circular shape) to maximize and direct the electrical field toward the nervous system structure.

In some embodiments, the stimulation device includes an elongated body portion sized and configured to be advanced through the nostril of the patient and along the middle nasal turbinate, where the electrode is provided at a distal end of the elongated body portion of the stimulation device, wherein the electrode has a contact surface having a size (e.g., a contact surface area 1.57 mm2 to about 56 mm2, a width between about 1 mm and about 6 mm) and shape (e.g., elongated triangular shape, a ball-tipped, or half-ball, or flat circular shape) corresponding to a size and shape of the SPG, such that the energy provided at the electrode can modulate the entire SPG simultaneously and the electrode can provide a uniform pressure on a mucosal layer proximate the SPG (e.g. a uniform pressure provided by the electrode applied via a transnasal approach).

In some embodiments, the elongated body portion extends between a proximal and distal end of the stimulation device such that the electrode is provided at a distal end of the elongated body portion, wherein the proximal end of the stimulation device extends through the nostril of the patient when the electrode is position adjacent the SPG, wherein a length of the elongated body portion ranges between about 5 cm and about 20 cm.

In some embodiments, elongated body portion includes a contour corresponding to a superior border of the middle nasal turbinate of a patient, wherein the elongated body portion is constructed from a material suitable for insertion through the nasal cavity of the patient (e.g., wherein the elongated body portion comprises a flexible material).

In some embodiments, the stimulation device is sized and configured to be positioned within the mouth of the patient (e.g., on a mouth piece fitted around the gums and/or teeth of the patient) such that the electrode is located on the gingival tissue (gum tissue) of the patient adjacent at least one of a ganglia or a peripheral nerve (e.g., a lingual nerve, an aleveolar nerve, a buccal nerve).

In some embodiments, the stimulation device is reusable.

In some embodiments, the stimulation device is disposable.

In some embodiments, the system includes a user interface (e.g., comprising a display (e.g., to provide an indication of status of the controller, stimulation device, patient), wherein the user interface is configured to receive an input from the user to direct the application of the electrical stimulation to the treatment site (e.g., to vary inhibition of the perception of pain (while preserving other sensory and motor function, and proprioception).

In some embodiments, the system includes a display coupled to at least one of the controller and the stimulation device, the display providing an indication of a status of the stimulation device.

In some embodiments, the controller is adjustable to vary the electrical stimulation based on a measured feedback selected from the group consisting of: measured inhibition of nerve signal transmission, measured temperature (e.g., at the treatment site, at the one or more electrodes or a portion thereof, at the electrical stimulation device, at the patient's skin), input from the patient (e.g., input regarding pain), a feedback corresponding to at least one of the adjustable parameters, a treatment setting associated with a time course of recovery, electrode contact impedance, electric field generated in the tissue, patient physiological response (e.g., blood flow, skin conductance, heart rate, muscle activity (e.g., such as electromyography)), and a combination thereof.

In some embodiments, the system includes a temperature sensor (e.g., thermistor) coupled to the stimulation device for measuring a temperature of at least one of i) a contact surface of the stimulation device and ii) the patient's tissue adjacent the contact surface or electrode, where the temperature sensor is coupled to the controller and provides thermal feedback information regarding a measured temperature, wherein the controller is adjustable to vary at least one parameter of the electrical stimulation (e.g. by the controller or by the user) in response to the thermal feedback information from the temperature sensor (e.g., to adjust a temperature of the contact surface to maintain the temperature of the patient's tissue (e.g., tissue comprising and surrounding the nervous system structure, mucosal tissue overlying the nervous system structure) below a destructive tissue temperature and/or maintain the temperature of the contact surface of the stimulation device/electrode below the destructive tissue temperature).

In some embodiments, the system includes at least one of a second temperature sensor coupled to an outer surface of the patient's skin, a blood flow meter for coupling to the outer surface of the patient's skin, a skin conductance meter coupled to the outer surface of the patient's skin, and a heart rate monitor for measuring the patient's heart rate, wherein the controller is adjustable to vary at least one parameter of the electrical stimulation (e.g. by the controller or by the user) in response to feedback information received from at least one of the second temperature sensor, the blood flow meter, the skin conductance meter, and the heart rate monitor, wherein the at least one adjustable parameter is selected from the group consisting of a waveform shape, a waveform frequency, a waveform amplitude, an electrical field strength generated at the electrode (e.g., measured at the electrode or at the treatment site), a waveform DC offset, a waveform duty cycle, a tissue temperature, a cooling mechanism parameter (e.g., a rate of cooling; a flow rate of cooling medium; cooling medium pressure; measured temperature at the second temperature sensor, treatment site, contact surface of the electrode, and/or at a portion of the cooling mechanism; and a treatment duration.

In some embodiments, the system includes a cooling mechanism configured to provide a cooling effect at the treatment site (e.g., contact surface of the stimulation device), wherein the cooling effect prevents damage (e.g., by pre-cooling and/or maintaining temperature when electrical stimulation is delivered) at the treatment site proximate the contact surface of the electrode (e.g., by preserving temperatures of the patient's tissue, including the mucosal tissue overlying the nervous system structure, below a destructive tissue threshold temperature).

In another aspect, a method is disclosed for modulating (e.g., selectively and and/or reversibly) targeted neural- and non-neural tissue of the sphenopalatine ganglion (SPG) with electrical stimulation (e.g., a single application of the electrical stimulation) to treat a medical condition of a patient. The method comprises locating a position of the SPG (e.g., using at least one of magnetic resonance imaging (MRI), fluoroscopy, and ultrasound imaging); advancing an electrical stimulation device transnasally to a treatment site proximate the neural and non-neural tissue of the sphenopalatine ganglion (SPG) of a patient, the stimulation device including an electrode sized and configured to be placed on a mucosal tissue overlying the SPG, the electrode generating an electric field for delivering an electrical stimulation to the treatment site sufficient to modulate the SPG and adjacent non-neural tissue; positioning the electrode at the treatment site; delivering an electrical stimulation to the treatment site via the electrode, wherein the application of the electrical stimulation to the treatment site modulates (e.g., selectively and/or reversibly modulates) the activity of the neural and non-neural tissue of the SPG inhibiting the perception of pain and preserving other sensory and motor function, and proprioception, and wherein the application of the electrical stimulation to the treatment side does not damage the mucosal tissue overlying the SPG.

In some embodiments, the pain comprises at least one of head-and-face pain, a migraine headache, a cluster headache, an occipital neuralgia, a tension headache, a sinus headache, cervicogenic headache, postherpetic neuralgia, post-traumatic pain, chronic daily headache (transformed migraine).

In some embodiments, the application of the electrical stimulation to the treatment site selectively modulates the neural- and non-neural tissue of the SPG inhibiting nerve signal transmission through nerve fibers that are responsible for the transmission of pain, wherein nerve signal transmission through nerve fibers responsible for other sensory and motor function, and proprioception is preserved, and wherein other sensory function includes at least one of touch, vision, audition, gustation, olfaction, and balance.

In some embodiments, the electrical stimulation delivered to the treatment site selectively modulates function of the neural- and non-neural tissue in and around the SPG such that the electrical stimulation selectively modulates a select type of nerve fiber of the SPG (e.g., parasympathetic fibers comprising the SPG sympathetic nerve fibers comprising the SPG, sensory nerve fibers comprising the SPG), inhibiting nerve signal transmission through the select type of nerve fiber, wherein function of at least one of a non-selected nerve fiber (e.g., parasympathetic nerve fibers, sympathetic nerve fibers, and sensory nerve fibers) is selectively preserved.

In some embodiments, the electrical stimulation delivered to the treatment site for modulating function of the SPG (e.g., nerve signal transmission through parasympathetic nerve fibers of the SPG) has a frequency of about 100 kHz to about 1 MHz, intensity ≤1,000 mA and ≤1,000 V (peak-to-peak), and an electrical field strength ≤1,000,000 V/m.

In some embodiments, the step of positioning the electrical stimulation device proximate the treatment site further comprises: delivering an initial electrical stimulation to the treatment site via the electrode; measuring at least one of a voltage and a current at the electrode; and adjusting a position of the electrode at the treatment site until the measured voltage and current corresponding to a threshold voltage and a threshold current, respectively.

In some embodiments, positioning the electrode at the treatment site comprises positioning the electrode adjacent a mucosal tissue overlying the SPG (e.g., the nasopharyngeal muscoa).

In some embodiments, positioning the electrode at the treatment site comprises positioning the electrode in contact with the mucosal tissue (e.g., securing the electrode to the mucosal tissue) overlying the SPG.

In some embodiments, the method further comprises confirming the position of the electrode at target site adjacent the mucosal tissue overlying the SPG (e.g., using magnetic resonance imaging (MRI), fluoroscopy, ultrasound imaging).

In some embodiments, the position of the electrode at the treatment site is confirmed by stimulating a biological response in the patient (e.g., a patient input regarding pain, a change and/or increase in cutaneous blood flow, a change and/or increase in skin conductance, a change and/or increase in heart rate).

In some embodiments, the method further comprises measuring at least one of a cutaneous blood flow change, a skin conductance change, and a heart rate change, wherein an increase in cutaneous blood flow is indicative of placement of the electrode adjacent the SPG, wherein an increase in skin conductance is indicative of placement of the electrode adjacent the SPG, wherein an increase in heart rate is indicative of placement of the electrode adjacent the SPG.

In some embodiments, the method further comprises adjusting at least one parameter of the electrical stimulation to selectively inhibit nerve signal transmission through the targeted neural- and non-neural tissue, wherein the at least one parameter is selected from the group consisting of a waveform shape, a waveform frequency, a waveform amplitude, an electrical field strength generated at the electrode (e.g., measured at the electrode or at the treatment site), a waveform DC offset, a waveform duty cycle, a tissue temperature, a cooling mechanism parameter (e.g., a rate of cooling, a flow rate of cooling medium, cooling medium pressure, measured temperature at the treatment site or at a portion of the cooling mechanism, and a treatment duration.

In some embodiments, the method further comprises adjusting the controller to vary the electrical stimulation based on a measured feedback selected from the group consisting of: measured inhibition of nerve signal transmission, measured temperature (e.g., at the treatment site, at the one or more electrodes or a portion thereof, or at the electrical stimulation device, at the patient's skin), input from the patient (e.g., input regarding pain), a feedback corresponding to at least one of the adjustable parameters, a treatment setting associated with a time course of recovery, electrode contact impedance, electric field generated in the tissue, patient physiological response (e.g., blood flow, skin conductance, heart rate, muscle activity (e.g., such as electromyography)), and a combination thereof.

In some embodiments, the electrode comprises a first and second electrode that operate independently, wherein delivering an electrical stimulation to the treatment site via the electrode further comprises delivering a first electrical simulation via the first electrode and delivering a second electrical stimulation via the second electrode, where the first and second electrical stimulations are intermittently outputted, where the first electrical stimulation is interleaved with respect to the second electrical stimulation such that an on cycle of the first electrical stimulation occurs during an off cycle of the second electrical stimulation and an on cycle of the second electrical stimulation occurs during an off cycle of the first electrical stimulation.

In some embodiments, the method further comprises measuring, at a thermistor, a temperature of at least one of a contact surface of the stimulation device and a patient's tissue adjacent the contact surface (e.g., a mucosal tissue overlying the SPG) during delivery of electrical stimulation, where the thermistor provides thermal feedback information regarding a measured temperature to the stimulation device; and adjusting the electrical stimulation (e.g., adjusting a parameter of the electrical stimulation) in response to the thermal feedback information received from the thermistor to create a cooling effect at a least one of the contact surface of the stimulation device and the patient's tissue adjacent the contact surface (e.g., to maintain a temperature of the mucosal tissue below a destructive tissue temperature and/or maintain a temperature of the contact surface below the destructive tissue temperature).

In some embodiments, the method further comprises measuring, at a thermistor, a temperature of at least one of a contact surface of the stimulation device and the patient's tissue adjacent the contact surface (e.g., a mucosal tissue overlying the SPG) during delivery of the electrical stimulation, wherein the thermistor provides thermal feedback information regarding the measured temperature to the stimulation device; activating a cooling mechanism to cool the contact surface of the stimulation device in response to the thermal feedback information received from the thermistor, where cooling the contact surface prevents damage to the patient's tissue when the electrical stimulation is delivered by preserving temperatures of the patient's tissue below a destructive tissue temperature; and activating the cooling mechanism to maintain the temperature of the contact surface of the stimulation device below the destructive tissue temperature in response to thermal feedback information regarding the measured temperature received from the thermistor.

In another aspect, a system is disclosed for modulating (e.g., selectively and and/or reversibly) targeted neural- and non-neural tissue of the sphenopalatine ganglion (SPG) to treat a medical condition of a patient. The system comprises an electrical stimulation device comprising an electrode sized and configured to be advanced percutaneously to a treatment site proximate the neural- and non-neural tissue of the SPG (e.g., the electrode having a size-, shape-, and contact-surface configuration suitable to deliver an electrical stimulation to the SPG and adjacent non-neural tissue) (e.g., monopolar or bipolar) (e.g., a single electrode or an array of electrodes), the electrode delivering an electrical stimulation to the treatment site; and a controller configured to connect to the electrode of the electrical stimulation device and to a power source configured to supply electrical energy to the electrode, where the controller is configured to direct operation of the electrical stimulation device (e.g., via current controlled, voltage controlled, power controlled, and/or temperature controlled) to apply the electrical stimulation to the treatment site through the electrode, wherein the application of the electrical stimulation to the treatment site selectively modulates the targeted neural- and non-neural tissue of the SPG, inhibiting the perception of pain and preserving other sensory and motor function, and proprioception, and wherein the application of the electrical stimulation to the treatment site does not damage the mucosal tissue.

In another aspect, a method is disclosed for modulating (e.g., selectively and and/or reversibly) targeted neural- and non-neural tissue of the sphenopalatine ganglion (SPG) with electrical stimulation (e.g., a single application of the electrical stimulation) to treat a medical condition of a patient. The method comprises locating a position of the SPG (e.g., using at least one of magnetic resonance imaging (MRI), fluoroscopy, and ultrasound imaging); advancing an electrical stimulation device percutaneously to a treatment site proximate the neural and non-neural tissue of the sphenopalatine ganglion (SPG) of a patient, the stimulation device including an electrode sized and configured to be placed adjacent SPG (e.g., near, in contact with, penetrating the SPG), the electrode generating an electric field for delivering an electrical stimulation to the target site sufficient to modulate the SPG and adjacent non-neural tissue; positioning the electrode at the treatment site; delivering an electrical stimulation to the treatment site via the electrode, wherein the application of the electrical stimulation to the treatment site modulates (e.g., selectively and/or reversibly modulates) the activity of the neural and non-neural tissue of the SPG inhibiting the perception of pain and preserving other sensory and motor function, and proprioception; and adjusting at least one parameter of the electrical stimulation to selectively inhibit nerve signal transmission through the targeted neural- and non-neural tissue, wherein the at least one parameter is selected from the group consisting of a waveform shape, a waveform frequency, a waveform amplitude, an electrical field strength generated at the electrode (e.g., measured at the electrode or at the treatment site), a waveform DC offset, a waveform duty cycle, a tissue temperature, a cooling mechanism parameter (e.g., a rate of cooling, a flow rate of cooling medium, cooling medium pressure, measured temperature at the treatment site or at a portion of the cooling mechanism, and a treatment duration, and wherein the application of the electrical stimulation to the treatment side does not damage the mucosal tissue overlying the SPG.

In another aspect, a non-transitory computer readable medium is disclosed. The computer readable medium having instructions stored thereon, wherein execution of the instructions by a processor causes the processor to perform any of the above-recited methods.

The details of one or more embodiments of the invention are set forth in the accompanying drawings and description below. Other features, objects, and advantages of the invention will be apparent from the description and drawings, and from the claims

BRIEF DESCRIPTION OF THE DRAWINGS

FIGS. 4B, 4C, 4D, 4E, 4F, 4G, 4H, 4I, 4J, 4K, 4L, 4M, 4N, 4O, and 4P each show a waveform shape for an electrical stimulation;

Like reference symbols in the various drawings indicate like elements.

Definitions

Figure 1:
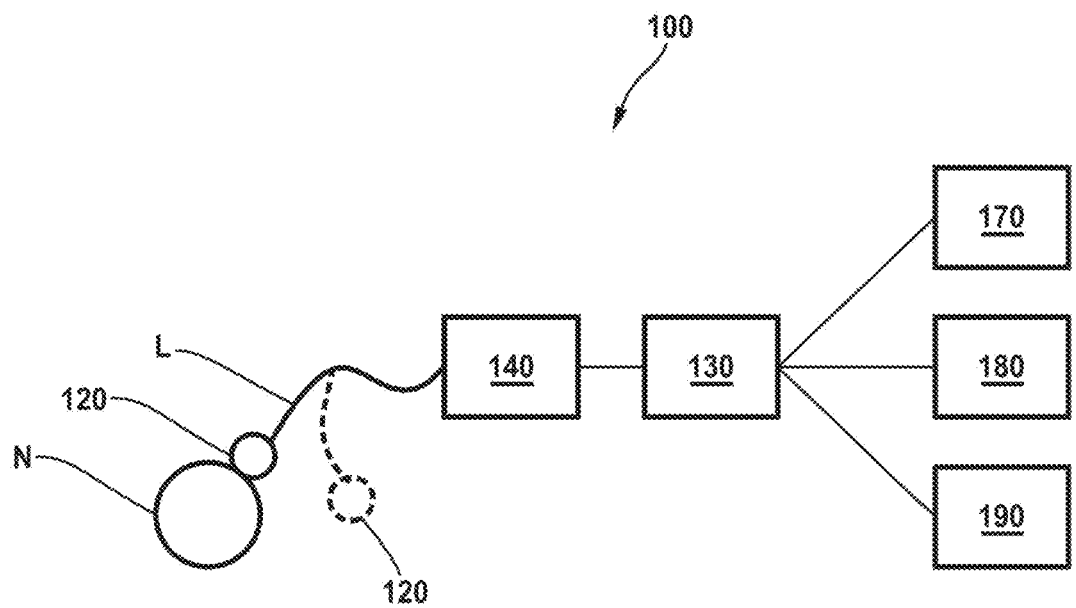
FIG. 1 is a schematic representation of an example electrical stimulation device.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

The terms "proximal" and "distal" are used herein as relative terms that refer to regions of a nerve, positions of nerves, or regions of a stimulation device. "Proximal" means a position closer to the spinal cord, brain, or central nervous system, whereas "distal" indicates a position farther from the spinal cord, brain, or central nervous system. When referring to the position on a neural structure in the peripheral nervous system or along an appendage, proximal and distal refer to positions either closer to the central nervous system or further from the central nervous system along the pathway followed by that neural structure or appendage. When referring to the position on a neural structure in the spinal cord, proximal and distal refer to positions either closer to the brain or further from the brain along the pathway followed by the neural structure.

Throughout the description and claims of this specification, the word "comprise" and variations of the word, such as "comprising" and "comprises," means "including but not limited to," and is not intended to exclude, for example, other additives, components, integers or steps. "Exemplary" and "e.g." means "an example of" and is not intended to convey an indication of a preferred or ideal aspect. "Such as" is not used in a restrictive sense, but for explanatory purposes.

As used herein, the term "nervous structure" or "neural structure" refers to a structure including neural and non-neural tissue. In addition to neural tissue (such as neurons and components of neurons including axons, cell bodies, dendrites and synapses of neurons), nervous structures may also include non-neural tissue such as glial cells, Schwann cells, myelin, immune cells, connective tissue, epithelial cells, neuroglial cells, astrocytes, microglial cells, ependymal cells, oligodendrocytes, satellite cells, cardiovascular cells, blood cells, etc.

As used herein, the term "stimulating electrode," also referred to in the case of monopolar stimulation as "the cathode", refers to an electrode responsible for delivering the therapeutic energy to the nerve. In the case of bipolar or multipolar stimulation, all of the electrical contacts are considered to be stimulating electrodes.

As used herein, "return electrode," also referred to in the case of monopolar stimulation as "the anode," refers to an electrode responsible for providing a return path for current that flows through the body. For example, the return electrode provides a return path for the current which is delivered to the target neural structure via the stimulating electrode.

As used herein, "electrical signal," "electric signal," "electrical simulation," "stimulation electric signal," "stimulation electrical signal" and "stimulation waveform" refer to the electrical signal delivered by the controller to the tissue by means of the stimulating electrodes or, in the case of monopolar stimulation by means of the stimulating electrode and the return electrode. For example, the electrical signal may be described as a temporally-varying voltage, current, power, or other electrical measure. The delivery of the electrical signal to the target tissue is referred to as an electrical treatment, an electrical therapy, or simply a treatment or a therapy. The electrical signal creates an electrical field in the tissue such that control of the electrical signal strongly influences control of the electrical field in the tissue.

As used herein, "treatment site" refers to the site on the neural and non-neural structure to which the electrical signal is delivered by means of the electrode(s).

As used herein, "modulate" refers to modifying or changing the transmission of information. For example, this includes both excitation, pacing, and inhibition/interruption of the passage of impulses along a neuron's axon within a nerve. Modulating nerve fiber activity includes inhibiting nerve signal transmission to the point of creating a blocking effect, including a partial and a complete blocking effect. Modulating nerve activity also includes modifying the trafficking of molecules such as macromolecules along the nerve fiber. Modulating nerve activity also includes changing downstream function of the neuron (for example at cell bodies and synapses), modifying signaling in a way that changes signaling in other neurons (for example neurons in the central nervous system such as the spinal cord or the brain), modifying the function of non-neural tissue in the neural structure, or otherwise modifying the processes, function, or activity in the target neural or non-neural tissue.

As used herein, the terms "inhibit" and "attenuate" refer to any level of reduction, including partial reduction or complete reduction of nerve signal activity through a nervous structure, e.g., the reduction of the passage of impulses along a neuron's axion within a nerve.

As used herein, "percutaneous" refers to electrical stimulation applied utilizing one or more electrodes penetrating through the surface of the skin so an electrode delivering electrical stimulation to a target nerve beneath the skin is also located beneath the skin. For percutaneous electrical stimulation, it is contemplated that return electrodes or anodes may be located beneath the skin or on the surface of the skin. The term "percutaneous electrode" refers to electrode assemblies inserted through the skin and directed into the vicinity of the nerve (mm to cm distance) in a minimally invasive fashion to electrically affect the physiology of the neural structure.

As used herein, the terms "pain sensation" or "painful sensation" refer to a disagreeable sensation generated, for example, by the activation of sensory nociceptors. Nociception describes the perception of acute pain and is generally caused by activation of sensory nociceptors or by disruption of nociceptor pathways (e.g. severed neurons or disrupted nociceptors). Chronic pain sensation can also be generated by activation of nerve fibers which result in a disagreeable perception similar in nature to that generated by activation of nociceptors (for example, neuropathic pain). In some cases, such as following a surgery intended to treat chronic pain, both acute pain sensation and chronic pain sensation may contribute in a mixed manner to the overall pain sensation.

As used herein, the term "target nerve" is synonymous with "neural structure" or "nervous structure", and refers, for example, to mixed nerves containing motor nerve fibers and sensory nerve fibers. It may additionally refer to sensory nerves containing only sensory nerve fibers and/or to motor nerves containing only motor nerve fibers.

As used herein, the terms "transmucosal" refers to electrical stimulation applied to the mucosal tissue overlaying a targeted nervous structure using one or more electrodes. The electrical stimulation passes through the mucosal tissue to the targeted nervous structure.

As used herein, the terms "preserve" or "preserving" refer to cases where nerve function is partially but not completely maintained, as well as cases where a function is completely maintained. In comparative cases, one function may be inhibited while another function is preserved, suggesting that, in a comparative sense, the inhibited function has experienced a magnitude of reduction greater than the magnitude of reduction experienced by the preserved function. Specifically, in comparative cases, inhibition of one function and preservation of another function does not require complete preservation or complete inhibition of either function or both functions.

DETAILED DESCRIPTION

Anatomy and Physiology

As provided above and as will be explained in more detail below, the present invention is directed to a device and method to selectively and reversibly modulate targeted neural- and non-neural tissue of a nervous structure by the application of an electrical signal to inhibit the perception of pain while preserving other sensory and motor function, and proprioception. The device and method can be used to treat acute pain (such as surgical pain, post-surgical pain, trauma pain), neuropathic pain, chronic pain, and head-and-face pain (such as migraine headache, cluster headache, an occipital neuralgia, tension headache, sinus headache, cervicogenic headache, postherpetic neuralgia, post-traumatic pain, chronic daily headache (transformed migraine)) via the application of an electrical signal to a targeted neural- and non-neural tissue of a nervous structure to modulate or inhibit nerve signaling.

Pain is a noxious perception generated in the conscious mind. In healthy humans, perception of pain is generated by activation of sensory nociceptors and subsequent transmission of nociceptive signaling to the brain along one or more neural pathways. Pain can be created by activation of a neural pathway, at any point along that neural pathway, that results in perception of pain. In healthy humans, pain-generating neural pathways are generally activated via sensory nociceptors, which are sensory nerve endings tuned to detect and signal noxious events (e.g. noxious mechanical or thermal damage to tissue). This type of pain generally represents a genuine noxious condition, and this type of pain subsides when the noxious condition is resolved. In cases where the noxious event is not a chronic tissue dysfunction, this type of pain is referred to as acute pain. In contrast, chronic pain represents conditions where pain-generating neural pathways are persistently modulated due to chronic tissue dysfunction or neural dysfunction. This may be due to genuine activation of sensory nociceptors at a site of chronically dysfunctional tissue or due to dysfunction of the neural tissue or tissue supporting the neural tissue that results in modulation at any point along pain-generating neural pathways.

Interventions to treat pain can be designed to either directly or indirectly modulate nerve signal transmission via pain-generating neural pathways at any level along these pathways. For example, direct blocking of axonal conduction in nerve fibers attached to sensory nociceptors can block perception of pain. As an additional example, indirect modulation of synaptic transmission in the spinal cord or nerve ganglia can be achieved by activating or blocking other inputs to the spinal cord or ganglia and may result in modulation along a pain-generating neural pathway. As another example, inhibition of parasympathetic outflow in the sphenopalatine ganglion can indirectly influence head and face pain, such as migraine, by modulating sensory input to the brain (for example via the superior salivatory nucleus). Thus, it is desired to target a variety of nervous structures when modulating and treating acute and chronic pain.

Targeted nervous structures include peripheral nerves (small diameter and large diameter), cranial nerves, ganglia, autonomic nerves, plexuses, and spinal cord. Ganglia comprise at least one of dorsal root ganglia, a sympathetic ganglia, a parasympathetic ganglia, a sphenopalatine ganglion, a gasserian ganglion, and autonomic ganglia in general. Generally, large peripheral nerves are those peripheral nerves having a diameter greater than about 2.5 mm. Example large peripheral nerves include, for example, the femoral nerve, sciatic nerve, vagus nerve, tibial nerve, peroneal nerve, median nerve, radial nerve, and ulnar nerve. Example small peripheral nerves include, for example, the saphenous nerve, sural nerve, genicular nerves, cranial nerves (such as trigeminal nerve and occipital nerve), obturator nerve, and distal portions of larger nerves (such as distal portions of the vagus, tibial, peroneal, median, radial, and ulnar nerves). Targeted ganglia can include dorsal root ganglia, sympathetic ganglia, parasympathetic ganglia, a sphenopalatine ganglion (SPG), a gasserian ganglion, plexuses, and the spinal cord. Each of these nervous structures includes neural tissue as well as non-neural tissue which supports the neural tissue and can influence transmission of information along pain-generating neural pathways. Example non-neural tissue can include, for example, glial cells, Schwann cells, myelin, immune cells, connective tissue, epithelial cells, neuroglial cells, astrocytes, microglial cells, ependymal cells, oligodendrocytes, satellite cells, cardiovascular cells, blood cells, etc. Neural tissue generally refers to neurons which include components such as axons, cell bodies, dendrites, receptor endings, receptors, and synapses.

Importantly, in the context of the present invention, modulation of neural tissue (neurons including components such as axons, cell bodies, dendrites, receptor endings, receptors, and synapses) and/or non-neural tissue (such as glial cells, Schwann cells, myelin, immune cells, connective tissue, neuroglial cells, astrocytes, microglial cells, ependymal cells, oligodendrocytes, satellite cells, cardiovascular cells, and blood cells, etc.) may be responsible in part or in whole for the therapeutic inhibition of perception of pain.

Peripheral nerves are primarily composed of axons, while other neural structures, such as ganglia and the spinal cord, include many components including axons, cell bodies, dendrites, and synapses. Within a nervous structure there is variability in the nature of these components, including, for example, variability in the size, shape, and interface with supporting non-neural tissue. For example, peripheral nerves often contain both large-diameter and small-diameter axons. Schwann cells are non-neural supporting cells which surround some axons and comprise an insulating cover rich in layers of lipid bilayers referred to as the myelin sheath. Some axons are surrounded by a myelin sheath, and some axons are not surrounded by a myelin sheath. Generally, the structure of different neural components is related to their function. For example, large-diameter axons typically transmit neural signals more-quickly than small-diameter axons due to the relatively large increase in axial conductance relative to a modest increase in membrane conductance as a function of diameter. Similarly, the presence of a myelin sheath on large-diameter axons further increases the speed of conduction velocity of the action potential by increasing the resistance to trans-membrane current flow between unmyelinated areas of the axon, referred to as nodes of Ranvier. Nodes of Ranvier are brief un-myelinated portions of the fibers; action potentials are relayed along the axon by a burst of trans-membrane current flow at each subsequent node of Ranvier. Peripheral nerve axons which generally transmit information from the periphery toward the central nervous system (e.g. sensory information including pain) are often referred to as afferent fibers, while axons which generally transmit information from the central nervous system toward the periphery (e.g. motor information) are often referred to as efferent fibers.

As used herein, the term "A fiber" refers to myelinated afferent or efferent peripheral axons of the somatic nervous system. Generally speaking, A fibers are associated with proprioception, somatic motor function, sensations of touch and pressure and also sensations of pain and temperature. A fibers generally have a diameter of about 1 to 22 micrometers ($\mu m$) and conduction velocities between about 2 meter per second (m/s) to more than 100 m/s. Each A fiber has dedicated Schwann cells forming the myelin sheath around the fiber. As described above, the myelin sheath has a high content of lipids, increasing the electrical resistance to trans-membrane current flow and contributes to the high conduction velocity of action potentials along the nerve fiber. A fibers include the alpha, beta, delta, and gamma fibers. The alpha, beta, and gamma A fibers have diameters ranging from 5 micrometers to 20 micrometers ($\mu m$) and are associated with motor function, low-threshold sensory function, and proprioception, but not pain. Delta A fibers are associated with pain, and have smaller diameters ranging from 1 micrometer to 5 micrometers (μm).

As used herein, the term "C-fiber" refers to non-myelinated peripheral axons of the somatic nervous system with conduction velocities of less than about 2 m/s. C fibers have a diameter of about 0.2 to 1.5 micrometers (μm) and include the dorsal root and sympathetic fibers and are primarily associated with sensations like pain and temperature, some limited mechanoreception, reflex responses, autonomic effector activity, and visceral function.

In a peripheral nerve, pain sensation that is perceived as dull and persistent is often referred to as 'slow pain' and is transmitted in peripheral nerves by C fibers which conduct neural signals relatively slowly. Pain sensation that is perceived as sharp and rapid is often referred to as 'fast pain' and is transmitted in peripheral nerves by Aδ fibers which have a higher conduction velocity than C fibers. Aδ fibers generally comprise small diameter sensory axons that are lightly myelinated, compared to the non-myelinated C fibers. Acute and chronic pain can involve both Aδ and C fibers.

In addition to the examples given for peripheral nerve axons, above, similar principles of structure and function for components of neural structures, such as axons, cell bodies, dendrites, receptor endings, receptors, and synapses apply for different neural structures including peripheral nerve, a cranial nerve, a ganglion, and an autonomic nerve, a plexus, and a spinal cord. The sub-cellular structures within components of non-neural and neural tissue, such as cell membranes, lipid bilayers, ion channels, mitochondria, microtubules, nucleus, vacuoles, and other components of the cytoplasm are also related to the function of such components of neural structures.

As another example, the sphenopalatine ganglion consists of parasympathetic neurons, sympathetic neurons, and sensory neurons. Within the sympathetic ganglion, cell bodies and synapses are present for the parasympathetic neurons, but not for the sympathetic or sensory neurons. Rather, only axons of the sympathetic and sensory neurons pass through the sphenopalatine ganglion. The present device and method can be used to selectively and/or reversibly modulate nerve signal transmission in one of the neural structure types (e.g. cell bodies, synapses, axons) while not modulating the other neural structures present in the ganglion. For example, modulation or inhibition of transmission via the parasympathetic neuron pathway, for example by inhibiting transmission of signals via the cell bodies or synapses in the sphenopalatine ganglion, can be achieved while preserving signaling via the sympathetic pathways and at least some of the sensory pathways. As an additional example, modulation or inhibition of transmission via the small-diameter sensory neurons can be achieved while preserving signaling via the sympathetic, parasympathetic, and other sensory fiber pathways. As another example, modulation of the parasympathetic pathway and the small-diameter sensory pathway can be achieved while preserving signaling via all other pathways in the ganglion. Notably, each type of neural component within a neural structure can have its own unique supporting non-neural tissue which contributes to the ability to selectively target modulation via specific pathways As will be described in more detail below, the present device and method can be used to selectively and reversibly modulate nerve signal transmission, for example by inhibiting or blocking nerve signal transmission, to inhibit the perception of pain. This selective and reversible inhibition of pain does not present risk of neural toxicity, vascular toxicity or injectable-chemical allergy. The present device is non-destructive of the target nervous structure and is suitable to treat chronic pain indications without the risks of atrophy, neuropathy and pain, and lends itself nicely to acute pain indications where nerve(s) are treated before, during, or soon after surgery so that the patient can go home without a device yet still experience pain relief for a period of day to weeks post-operatively, such as after a joint replacement or other orthopedic procedure. In other words, a device in which long-term, direct contact with the target area or nerve to be treated (e.g., via an implantable generator and a nerve cuff) is not required. However, if desired and especially for chronic pain indications, the device may still be implanted or partially implanted and/or carried home with the patient.

Example Device

FIG. 1 provides a schematic representation of an example electrical stimulation device 100. The electrical stimulation device 100 can be used to selectively and reversibly modulate a targeted neural- and non-neural tissue of a nervous structure with application of an electrical signal to treat a medical condition of a patient. The stimulation device 100 comprises an electrode 120 that delivers electrical stimulation to the treatment site, e.g., delivers the electrical stimulation to the targeted neural and non-neural tissue of the nervous structure. The electrical stimulation can be delivered by a percutaneously-placed lead (L) and electrode 120, by an implanted lead (L) and electrode 120, or by an electrode 120 advanced through a body opening and positioned adjacent (e.g., near or in contact with) the mucosal tissue overlying the targeted nervous structure (e.g., sphenopalatine ganglion, gasserian ganglion). Example wherein the mucosal tissues include an oral mucosa, a nasal oral mucosa, a gastrointestinal (GI) tract mucosa, a bowel mucosa, a bladder mucosa. The electrode 120 generates an electric field at the treatment site that results in selective and reversible modulation of the nerve fiber activity to inhibit the perception of pain. As provided above, the "modulation" of nerve fiber activity includes both the excitation and inhibition/interruption the passage of impulses along a neuron's axon within a nerve and can include inhibiting nerve signal transmission to the point of creating a blocking effect.

The delivery of the electrical signal stimulation includes interactions with other nearby tissues. For example, in the case of percutaneous application and positioning of the electrode, the electrical signal stimulation is delivered via the electrode 120 which has penetrated and navigated through the patient's outer tissues, including their skin, fat, bone, and muscle, in order to provide placement of the electrode 120 proximate a target nervous structure. In this example, the electrical stimulation influences not only the target neural structure, but also surrounding tissue such as connective tissue, supporting tissues of the nervous structure, fat, bone, muscle, and cardiovascular tissues and cells such as those present in and around blood vessels. In the case of transmucosal application, the electrical signal stimulation is delivered via the electrode 120 which is placed adjacent (e.g., near or in contact with) the overlying mucosal tissue. The electrical stimulation may affect targeted nervous structure, as well as the tissues beneath and surrounding the electrode 120, the tissues interposed between the electrode 120 and the target nervous structure, as well as other surrounding tissues (including skin, fat, muscle, bone, cartilage, connective tissue, supporting tissues of the nervous structure, cardiovascular tissues and cells such as those present in and around blood vessels, as well as other tissues present in the epidermis, dermis, as well as nerve receptors, hair follicles, sweat glands, sebaceous glands, apocrine glands, and lymphatic vessels). While application of the electrical stimulation to treatment site, in both the percutaneous and transnasal application, will modulate (e.g., selectively and/or reversibly, the targeted neural- and non-neural tissue of the nervous system structure to inhibit the perception of pain, the electrical stimulation and stimulation device 100 are designed such that no damage is caused to the nervous system structure and/or the surrounding tissue (e.g., the overlying mucosal tissue).

Figure 2A:
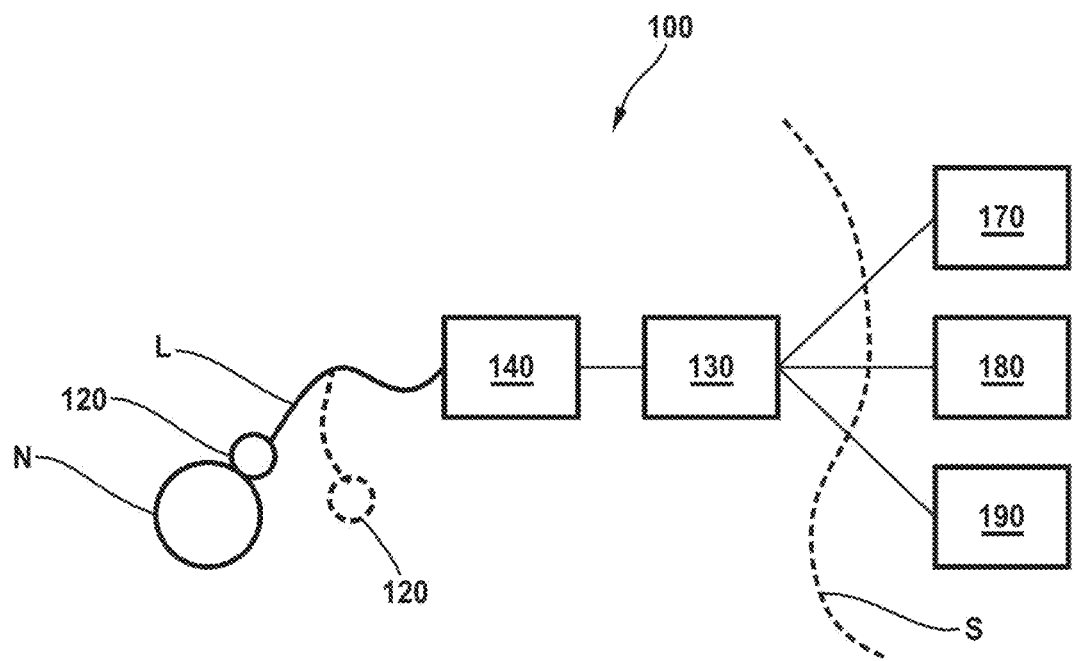
FIG. 2A is a schematic representation of the electrical stimulation device of FIG. 1.
Figure 2B:
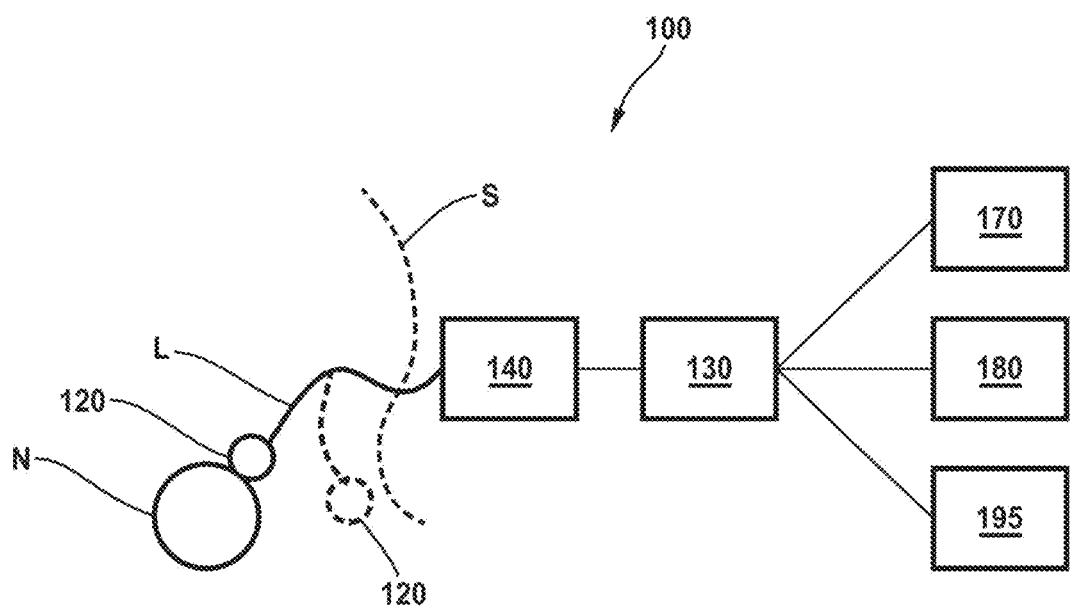
FIG. 2B is a schematic representation of the electrical stimulation device of FIG. 1.

As schematically illustrated in FIG. 1, the stimulation device 100 and electrode 120/leads L may be either reusable or disposable. Desirably, the nervous structure can be modulated via a disposable lead L and electrode 120, and driven by a reusable external stimulator/signal generator 140 and controller 130. It is contemplated that the stimulation device 100, in its entirety, can be sized and configured for implantation within the patient (under the patient's skin (S)) at a location adjacent the targeted nervous structure (N), represented schematically in FIG. 2A. The power source 180, providing electrical energy to the controller 130/signal generator 140 can be positioned internal or external to the patient. It is also contemplated that only the leads/electrode 120 be implanted within the patient and the remaining components, including signal generator 140 and controller 130 are embodied in a handheld device that can be easily manipulated to deliver the therapy, represented schematically in FIG. 2B. It is further contemplated that the stimulation device 100, including signal generator 140, controller 130, and leads/electrodes 120 may be embodied in a larger, non-handheld device designed to remain on a stationary surface or on a cart that can be moved between rooms at a medical clinic, any only the electrodes 120/leads (L) are advanced percutaneously through an opening in the patient's skin or other opening in the patient's body (e.g., via the nasal cavity).

The simulation device 100 can be used to reversibly and/or selectively inhibit pain perception while preserving other sensory function. Specifically, the electrical stimulation provided by the stimulation device 100 may reversibly and/or selectively modulate nerve signal transmissions through nerve fibers that are responsible for the transmission of pain while preserving nerve signal transmission through nerve fibers responsible for other sensory and motor function, and proprioception.

With respect to the reversibility of the modulated nerve function, the stimulation device 100 can reversibly inhibit perception of pain, for example by inhibiting or blocking nerve signal transmission for a period of about 1 day to about 30 days. Preferably, pain perception is inhibited for a period of about 5 days to about 30 days. Reversibility of nerve signal transmission and subsequent recovery of function after the appropriate duration of time from treatment is important, particularly for post-surgical acute pain. The parameters of the stimulation waveform can be adjusted to tune the expected duration of pain inhibition and to ensure that pain inhibition does not last for longer than is desired. For example, in patients undergoing knee replacement surgery, it is important for pain perception to return 15-30 days post-surgery because acute pain sensations serve an important protective signal to help patients regulate their physical activity during recovery.

With respect to the selectively of the modulated nerve function, the stimulation device 100 can selectively modulate the neural- and non-neural tissue inhibiting the perception of pain and preserving other sensory and motor function, and proprioception. This produces a scenario in which the electrical neuromodulation treatment is selective to a subset of functions of a nervous structure while preserving other functions of the nervous structure. Pain perception is inhibited, while other sensory and motor function, and proprioception is preserved. For example, the electrical signal disrupts the transmission of pain signals that originate in the periphery from reaching the brain by inhibiting nerve signal transmission through nerve fibers that are responsible for the transmission of pain. This includes direct inhibition of transmission of pain signals in the neurons of the target neural structure, or can be achieved by indirect inhibition of other downstream neurons responsible for transmitting pain signals to the brain, such as neurons of the central nervous system (e.g. spinal cord and the brain).

Preserved sensory function includes, for example, non-painful touch sensation (low-threshold sensory function), vision, audition, gustation, olfaction, and balance. It is also contemplated that the disclosed electrical signal can modulate nerve signal transmission through nerve fibers responsible for the transmission of thermoreception, autonomic effector activity and visceral function.

Selective modulation of perception of pain is particularly useful in cases where the modulation is desired to be applied to mixed nervous structures, such as peripheral nerves containing motor and sensory axons. For example in many surgical interventions, it is desirable to modulate pain transmitted via mixed nerves to treat acute surgical pain, while preserving motor and sensory and proprioceptive function of the nerve. Preservation of motor and sensory and proprioceptive function while treating pain is particularly important in cases where physical therapy or other movement of an appendage needs to be performed during recovery from surgery. For example, many post-surgical care programs include steps to help patients avoid muscle atrophy or other stagnation of function after surgical procedures. Preservation of motor control and sensory and proprioceptive function while treating pain can enable and enhance such programs.

As is described in more detail below, one or more parameters of the electrical stimulation can be adjusted to selectively block nerve signal transmission through a select type of nerve fiber and/or through a select region of the nervous structure. Adjustable parameters of the electrical stimulation include, for example, a waveform shape, a waveform frequency, a waveform amplitude, an electrical field strength generated at the electrode 120 (e.g., measured at the electrode or at the treatment site), a waveform DC offset, a waveform duty cycle (e.g., a continuous delivery and/or intermittent delivery through the electrode), a tissue temperature, a cooling mechanism parameter (e.g., a rate of cooling, flow rate of cooling medium, cooling medium pressure, measured temperature at treatment site or a portion of cooling mechanism), and a treatment duration. These parameters are adjustable and controllable by means of the controller 130, the user interface 170, and a cooling mechanism that may be incorporated into the stimulation device 100, as is described in more detail below.

For example, where the targeted nervous structure is a large peripheral nerve, e.g., a nerve having a diameter greater than about 2.5 mm, the electrical stimulation can inhibit nerve signal transmission through the myelinated Aδ fibers and/or the unmyelinated C fibers in the peripheral nerve, where the electrical stimulation preserves nerve signal transmission through at least one of the Aβ and Aα fibers, and/or motor fibers. It is contemplated that at least one parameter of the electrical stimulation can be adjusted to selectively inhibit the myelinated Aδ fibers and/or the unmyelinated C fibers, while preserving nerve signal transmission through at least one of the Aβ and Aα fibers, and/or motor fibers.

In another example, the targeted nervous structure covered by a layer of mucosal tissue, e.g., the gasserian ganglion, sphenopalatine ganglion (SPG). The electrical stimulation can be delivered through the mucosal tissue to modulate nerve single transmission through a particular type of nerve fibers of the underlying nervous structure and adjacent non-neural tissue. Types of nerve fibers including, for example, parasympathetic nerve fibers, sympathetic nerve fibers, the sensory nerve fibers). For example, where the targeted nervous structure includes the sphenopalatine ganglion (SPG), the electrical stimulation selectively inhibits nerve signal transmission through the parasympathetic nerve fibers comprising the SPG, the sympathetic nerve fibers comprising the SPG, and/or the sensory nerve fibers comprising the SPG. It is contemplated that this nerve signal transmission can be inhibited while also selectively preserving function of at least one of the non-selected type of nerve fiber (e.g., parasympathetic, sympathetic, and sensory nerve fibers comprising the SPG).

It is further contemplated that at least one parameter of the electrical stimulation can be adjusted to differentially inhibit function of the myelinated Aδ fibers such that the myelinated Aδ fibers have a larger percentage of fibers inhibited than the unmyelinated C fibers. Nerve signal transmission through myelinated Aδ is typically associated with the sensation of fast, sharp/stabbing pain, while nerve signal transmission through unmyelinated C fibers is typically associated with the sensation of dull/aching pain. Accordingly, the electrical stimulation can be adjusted to differentially inhibit the function of nerve fibers responsible for the sensation of sharp pain, such that those fibers have a larger percentage of fibers inhibited than nerve fibers responsible for the sensation of dull/aching pain Similarly, it is further contemplated that at least one parameter of the electrical stimulation can be adjusted to differentially inhibit function of the unmyelinated C fibers, such that the unmyelinated C fibers have a larger percentage of fibers inhibited than the myelinated Aδ fibers. That is, the electrical stimulation can be adjusted to differentially inhibit the function of nerve fibers responsible for a sensation of dull/aching pain, such that those fibers have a larger percentage of fibers inhibited than nerve fibers responsible for a sensation of fast, sharp/stabbing pain.

In another example, where the targeted nervous structure covered by a layer of mucosal tissue, such as the gasserian ganglion or sphenopalatine ganglion (SPG), the electrical stimulation can be adjusted to differentially inhibit function of the parasympathetic, sympathetic, and/or sensory nerve fibers of the ganglion. For example, the electrical stimulation delivered to the target site can differentially inhibit the function of the parasympathetic nerve fibers of the SPG, where the parasympathetic nerve fibers have a larger percentage of fibers inhibited than non-parasympathetic nerve fibers and the non-neural tissue. Likewise, the electrical stimulation delivered to the target site can differentially inhibit the function of the sympathetic nerve fibers of the SPG, where the sympathetic nerve fibers have a larger percentage of fibers inhibited than non-sympathetic fibers and the non-neural tissue. Similarly, the electrical stimulation delivered to the treatment site can differentially inhibit function of the sensory nerve fibers of the SPG, where the sensory nerve fibers have a larger percentage of fibers inhibited that the parasympathetic, sympathetic and the non-neural tissue.

An additional mechanism of inhibition of perception of pain is when the inhibitory effect is downstream or secondary to the treatment site. For example, where the targeted nervous structure is a large peripheral nerve, e.g., a nerve having a diameter greater than about 2.5 mm, the electrical stimulation can modulate activity or function of neural or non-neural tissues which results in activation of a biochemical signaling cascade which causes a decrease in activation of spinal or cortical neurons representing pain (for example, via modulation of synaptic signaling), while nerve signal transmission through central nervous system and peripheral nervous system neurons involved in detection, transmission, processing, and generation of non-painful touch, motor control, and proprioception are preserved. It is contemplated in this case, that at least one parameter of the electrical stimulation can be adjusted to selectively inhibit downstream or secondary effects of pain originating from Aδ fibers and/or originating from the unmyelinated C fibers, while the function of central nervous system and peripheral nervous system neurons involved in detection, transmission, processing, and generation of non-painful touch, motor control, and proprioception are preserved.

It is further contemplated in this case that at least one parameter of the electrical stimulation can be adjusted to differentially inhibit downstream or secondary effects of pain originating from myelinated Aδ fibers such that the downstream or secondary effects from myelinated Aδ fibers are inhibited to a greater extent than the downstream or secondary effects from unmyelinated C fibers. Similarly, it is further contemplated in this case that at least one parameter of the electrical stimulation can be adjusted to differentially inhibit downstream or secondary effects of pain originating from unmyelinated C fibers, such that the downstream or secondary effects from unmyelinated C fibers are inhibited to a greater extent than the downstream or secondary effects from myelinated Aδ fibers.

Example Electrical Stimulation

As described above, the electrode 120 provides an electrical signal to the treatment site for selectively modulating the neural- and non-neural tissue inhibiting the perception of pain and preserving other sensory and motor function, and proprioception. The electrical signal disrupts the transmission of pain signals by modulating both neural and non-neural tissue. Various parameters of the electrical signal can be adjusted, as outlined below, to modulate function via the nervous structure, including, for example, a stimulation-pulsed waveform shape (also referred to herein simply as "waveform shape"), a stimulation-pulsed frequency (also referred to herein simply as "frequency"), a stimulation-pulsed amplitude (also referred to herein simply as "amplitude"), an electrical field strength generated at the electrode 120, a stimulation-pulsed waveform DC offset, a waveform duty cycle (e.g., a continuous delivery, and/or intermittent delivery through the electrode), a tissue temperature, a cooling mechanism parameter, and a treatment duration. It is contemplated that some parameters may be adjusted individually to produced a desired effect, while others are adjusted in combination with some interdependence on each parameters adjustment in an effect to produce the desired effect. As described above, and in more detail below, various parameters and/or combinations of parameters of the electrical signal are adjusted to selectively and reversibly modulate nerve signal transmission through a select type of nerve fiber and/or through a select region of the nervous structure.

To facilitate the selective and/or reversible inhibition of nervous system activities (e.g., to block acute pain), the stimulation device and system is configured, in some embodiments, to apply a high frequency stimulation directly to the nerve and/or to nearby tissue to invoke sufficient pain inhibition response by the nervous system. The high-frequency stimulation may be applied in pulses over the course of a single treatment/application and in a manner so as to avoid damaging nearby tissue and nerve tissue. It has been observed that a high-frequency stimulation applied at 500 kHz in a series of 20 millisecond pulse at up to 100 V for a few minutes (and up to a temperature of 42° C.) can be applied to invoke a sufficient pain inhibition response that can selectively disrupt sensation of acute pain but not affect other neurological function such as motor control. It has also been observed that the same high-frequency stimulation can be applied to invoke a reversible pain inhibition response in that pain is blocked for a clinically relevant duration that can last from 1 day to 30 days. Without wishing to be bound to a particular theory, it is hypothesized that the selective and reversible effect can be attributed to the particularly high voltage-field that is applied to the tissue while not causing thermal damage at the treatment site, particularly to the nerves.

Figure 4A:
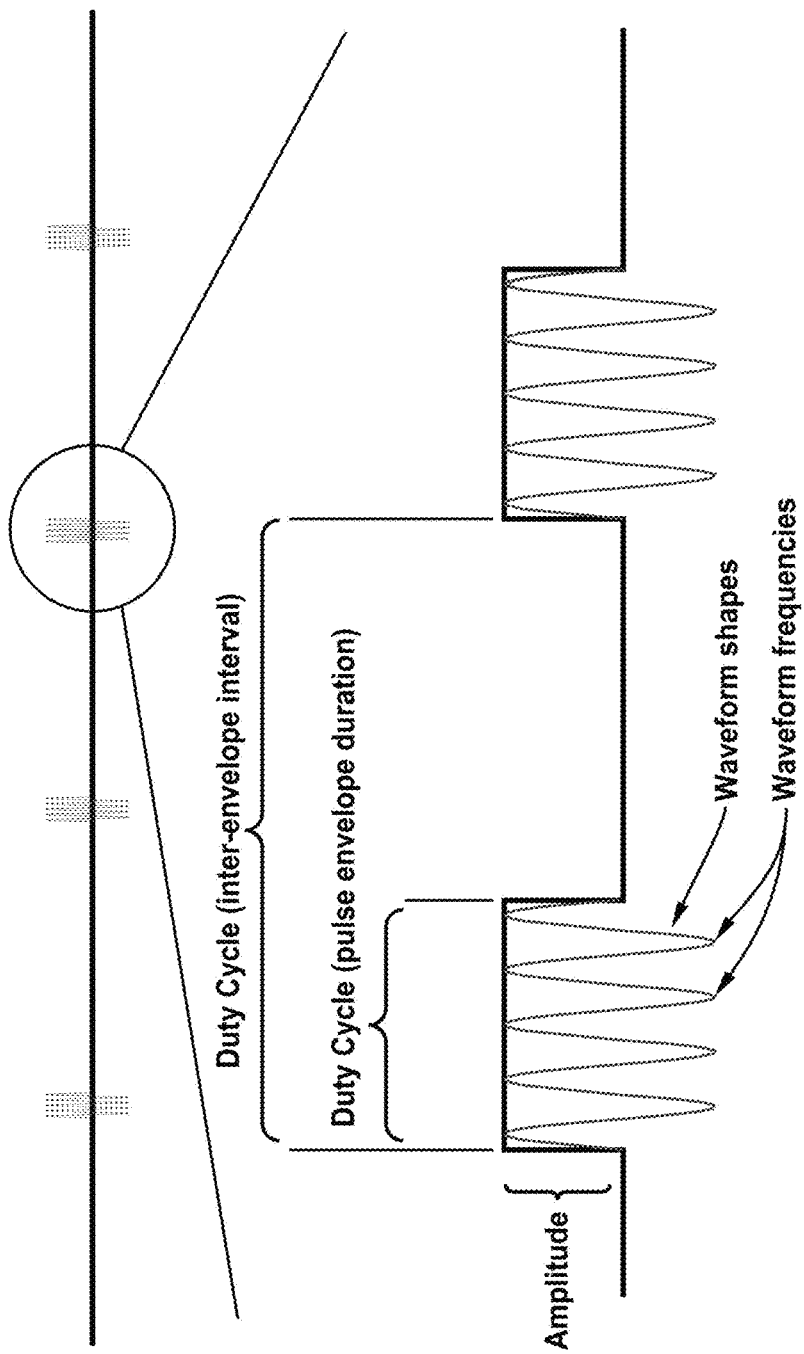
FIG. 4A is an example electrical stimulation, and corresponding control parameters, that can be applied to the nerve and/or nearby tissue to selectively and/or reversibly inhibit nervous system activities.

FIG. 4A shows an example electrical stimulation, and corresponding control parameters, that can be applied to the nerve and/or nearby tissue to selectively and/or reversibly inhibit nervous system activities, in accordance with an illustrative embodiment. As shown in FIG. 4A, the electrical stimulation can be defined via control parameters such as amplitude, pulse duty cycle (e.g., comprising a pulse envelope duration and an inter-envelope interval), stimulation waveform shape, and waveform frequency. In addition to a stimulation frequency of 500 kHz, other stimulation frequency ranges can be applied. In some embodiments, the stimulation device and system is configured to apply an electrical stimulation having a stimulation frequency selected from the group consisting of about 100 kHz, about 150 kHz, about 200 kHz, about 250 kHz, about 300 kHz, about 350 kHz, about 400 kHz, about 450 kHz, about 500 kHz, about 550 kHz, about 600 kHz, about 650 kHz, about 700 kHz, about 800 kHz, about 850 kHz, about 900 kHz, about 950 kHz, and about 1 MHz. Application of an electrical stimulation having a pulse duty cycle can allow for a higher voltage or current amplitude to be outputted and/or higher frequency (to allow for higher voltage field to be generated at the treatment site) while not causing thermal damage at the tissue. Application of an electrical stimulation having a non-sinusoidal waveform can be used to adjust the energy density that is applied in a given electrical stimulation and/or also allowing for higher electrical field to be applied.

Figure 4G:
Figure 4H:
Figure 4I:
Figure 4J:
Figure 4N:
Figure 4O:
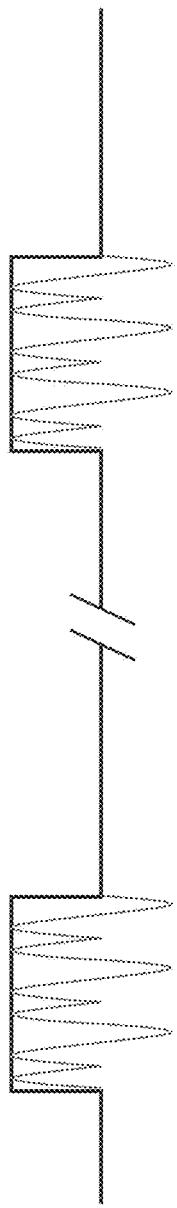
Figure 4P:
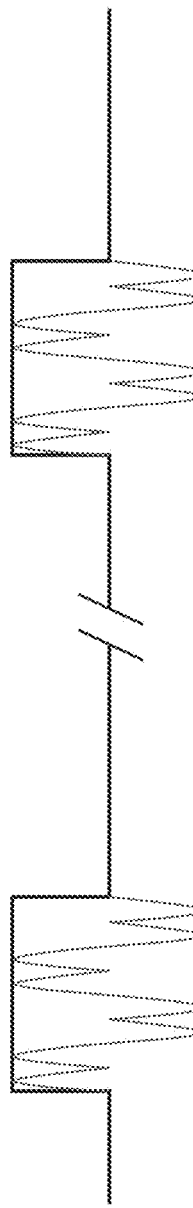

FIGS. 4B, 4C, 4D, 4E, 4F, 4G, 4H, 4I, 4J, 4K, 4L, 4M, 4N, 4O, and 4P each shows a waveform shape for an electrical stimulation, in accordance with an illustrative embodiment. As shown in FIGS. 4B-4F, in some embodiments, the stimulation waveform is a sinusoidal waveform (FIGS. 4B, 4G), a triangular waveform (FIG. 4C), a square or rectangular waveform (FIG. 4D), a triangular saw-tooth waveform (FIG. 4E), or a complex waveform (FIG. 4F).

In some embodiments, the frequency of a given pulse is varied (e.g., as a chirp, as shown in FIGS. 4K, 4L, and 4M). In some embodiments, the amplitude envelope of the electrical stimulation is varied for a given pulse (FIGS. 4K and 4L).

In some embodiments, the electrical stimulation is a voltage controlled output. In some embodiments, the electrical stimulation is a current controlled output. In some embodiments, the electrical stimulation is a power controlled output.

In some embodiments, the stimulation waveform shape comprises a continuous charge-balanced sinusoid (see, e.g., FIGS. 4B-4F, 4K, 4L, 4M, 4N, and 4P), or an additive combination of sinusoids (e.g., as a sine function (see FIGS. 4N, 4O, and 4P)).

The illustrated waveforms are merely illustrative. It is contemplated that other type of waveforms shapes can be generated such as impulses or other shapes. In some embodiments, the stimulation waveform comprises a single pulse having a duration of 1 µs to 10 µs.

Other stimulation pulse control parameters can be controlled, e.g., in a feedback mechanisms, such as electric field strength at the electrode, DC offset, tissue temperature, cooling mechanism parameter, and treatment duration. In some embodiments, the stimulation device and system is configured to control the electrical stimulation based on an observed or measured temporal and/or spatial derivatives of voltage, current, power, and temperature (e.g., the rate-of-change of temperature over time). In some embodiments, two or more of current-controlled stimulation, voltage-controlled stimulation, power-controlled stimulation, and temperature-controlled stimulation can be executed in combination to deliver to the targeted neural- and non-neural tissue of the nervous structure. The parameters of amplitude, waveform shape, frequency, DC offset, duty cycle and duration can be tuned for such current-controlled stimulation, voltage-controlled stimulation, power-controlled stimulation, and/or temperature-controlled stimulation, or a combination thereof.

Indeed, the stimulation parameters can be optimized to selectively inhibit perception of pain while preserving nerve activity responsible for motor activity, low-threshold sensory function, and proprioception. For example, the stimulation parameters can be optimized to attenuate or abolish activity in myelinated Aδ and unmyelinated C fibers while preserving (e.g., without attenuating) nerve activity in the nerve fibers responsible for motor activity, low-threshold sensory function, or proprioception.

The amplitude and other parameters of the stimulation waveform may be tuned to preferentially or optimally modulate activity within a desired region of a nerve (e.g., affect specific regions of a nerve vs. affecting the complete nerve cross-section), as will be described in more detail below. The stimulation waveform can also include parameter changes which influence and reduce onset response (e.g., a pulsing sensation at the nervous structure, motor response in a muscle adjacent the target nerve such as muscle spasm or twitching) and activation of nerve tissue at the onset of stimulation at either the beginning of the continuous waveform or at the onset of each burst of stimulation during intermittent stimulation. The parameters of the stimulation waveform may also be tuned to control the duration and time-course of pain inhibition that will be achieved after the treatment and to ensure that adequate pain inhibition is achieved with a single treatment.

The parameters of the stimulation waveform may be adjusted to enable treatment of larger nerves (for example, with a diameter greater than about 2.5 mm) and larger nervous structures or nervous structures with different shapes, sizes, and neural and non-neural tissue composition, for example by increasing the amplitude or adjusting other parameters of the stimulation waveform which result in an increase in the spatial size and shape electric field. Some nervous structures, such as the spinal cord and some ganglia or plexuses, are large by nature and treatment of these large structures is enabled by adjustment of the waveform parameters.

The parameters of the stimulation waveform may also be adjusted to enable non-damaging treatment and inhibition of pain. Hardware and software may also be included to control the amount of DC current delivered concurrently with the waveform. The controller 130 may include, for example, a current controller or a voltage controller for adjusting the amount of DC current or voltage delivered concurrently with the electrical signal.

The present device and method can be used to selectively and reversibly modulate nerve signal transmission, for example by inhibiting or blocking nerve signal transmission, to inhibit the perception of pain for a period of about 1 day to about 30 days. Preferably, pain perception is inhibited for a period of about 5 days to about 30 days. Reversibility of nerve signal transmission and subsequent recovery of function after the appropriate duration of time from treatment is important, particularly for post-surgical acute pain. The parameters of the stimulation waveform can be adjusted to tune the expected duration of pain inhibition and to ensure that pain inhibition does not last for longer than is desired. In one example, the duty cycle, pulse amplitude, and treatment duration (see e.g., FIGS. 7 and 8) can be adjusted to produce a desired reversibility of the nerve signal inhibition (see e.g., FIGS. 7 and 8). In another example, controlling the temperature at the treatment site can be used to produce a desired selectivity of the modulation of nerve signal transmission (see e.g., FIGS. 7 and 8).

As mentioned above, the device and method of the present invention, including the parameters of the waveform and adjustment thereof, can selectively inhibit acute pain (such as post-surgical pain) for a period of days-to-weeks post-procedure. However, it is also to be understood that the device and method of the present invention, including the parameters of the waveform and adjustment thereof, can also be used to provide therapeutic treatment for chronic pain conditions. The therapeutic treatment for chronic pain may include ongoing preventative delivery of signals, or abortive, on-demand delivery when episodes of chronic pain are experienced. This may be performed via percutaneous, partially-implanted, and implanted approaches.

Compared to other methods of modulating activity of a nervous structure using an electrical signal, the system and method of the present disclosure is able to provide selective and reversible pain relief for periods of days to weeks with a single treatment/application of the electrical signal. Other treatment modalities require repeated treatments over a period of days to provide any meaningful and lasting pain relief, particularly with respect to the treatment of large nerves. For example, pulsed radiofrequency, frequently used to treat pain in small nerves, utilizes intermittent pulses of a 45V radiofrequency signal to stimulate the target nerve. Pulsing is used in this case to avoid temperatures at the treatment site that would damage or destroy the nerve tissue. In contrast, the stimulation parameters of the present disclosure allow for the application of a high voltage, high frequency waveform that does not have the temperature limitations associated with a pulsed RF signal. Adjustment of the parameters of the stimulation waveform enables control of the application of the electric signal to ensure that adequate pain inhibition is achieved with a single application while avoiding damage to the tissue.

For example, a system can be configured to deliver the electrical signal (also referred to herein as "electrical stimulation") to the treatment site with a frequency range between of about 100 kHz to about 1 MHz, between about 200 kHz to about 800 kHz, between about 400 kHz to about 600 kHz, and between about 450 kHz to about 550 kHz. In an example system, the electrical stimulation delivered to the treatment site is at least 500 kHz. The electrical signal delivered to the treatment site has an amplitude range ≥50 mA (peak-to-center, corresponding to 100 mA peak-to-peak) and ≤2.5 A (peak-to-center, corresponding to 2.5 A peak-to-peak). In an example system, the electrical signal has an amplitude ranging between 50 mA and 500 mA, 500 mA and 1 A, 1 A and 1.5 A, 1.5 A and 2 A, or 2 A and 2.5 A. In an example system where the electrical simulation is delivered transmucosally, the electrical signal has an amplitude ranging between about 10 mA and about 5,000 mA (peak-to-peak). The electrical signal delivered to the treatment site has an amplitude range ≥10 V and ≤500 V (peak-to-center, corresponding to 100-1000 V peak-to-peak). In an example system, the electrical signal has an amplitude ranging between 10 V and 1,000 V, 20 V and 100 V, 100 V and 200 V, 200 V and 300 V, 300 V and 400 V, or 400 V and 500 V. In an example system where the electrical simulation is delivered transmucosally, the electrical signal delivered to the treatment site has an amplitude range ≥10 V and ≤1,000 V (peak-to-peak). In an example system, the electrical stimulation delivered to the treatment site has a power ranging between about 1 W and about 1,250 W.

The electrical signal delivered to the treatment site can have a sinusoidal shaped waveform, a square shaped waveform, a triangular shaped waveform, a frequency-modulated waveform, an impulse (e.g., an amplitude-modulated waveform, or an impulse-shaped waveform), and/or additive combinations thereof. An example of a frequency-modulated waveform is a chirp. An example of an amplitude-modulated waveform is a wavelet. In another example system, the electrical signal delivered to the treatment site has an arbitrary waveform. In another example system the electrical signal can have a combination of the waveforms mentioned previously. Repeated delivery of the waveform is implied in which a waveform shape is delivered in repeated fashion at a specified repetition frequency. The waveform of the electrical signal can be delivered continuously or intermittently. Continuous delivery implies that the waveform is delivered at a specified waveform frequency continuously, without breaks. Intermittent delivery implies that the waveform is delivered at a specified waveform frequency during envelopes of time that are separated by breaks during which no stimulation is delivered. For continuous delivery, the duty cycle is 100% (for example, via chirp function). For intermittent delivery, the duty cycle ranges from about 0.1% to about 99%, preferably 0.5% to 25%. The term duty cycle refers to a period that the pulse is on having multiple oscillations with a predefined frequency. For intermittent delivery, the electrical signal has an inter-envelope width of about 1 ms to about 999 ms, preferably 70-999 ms, where the inter-envelope width is defined as the duration of time between then end of an envelope and the start of the next envelope. In one example, the electrical signal has a 30 ms pulse width delivered at 10 kHz.

During an example treatment, the electrical signal is delivered for a treatment duration of ≤30 minutes, preferentially ≤15 minutes. In an example system, the electrical signal is delivered for treatment duration of ≤1 minute, 1 minute to 5 minutes, 5 minutes to 10 minutes, 10 minutes to 15 minutes, 15 minutes to 20 minutes, 20 minutes to 25 minutes, or 25 minutes to 30 minutes.

As described below, the controller 130 is adjustable to apply the electrical stimulation while maintaining the tissue temperature between about 5° C. and about 60° C. That is, the electrical signal can have a tissue temperature that has an amplitude between about 5° C. and about 60° C.

The electrical signal delivered to the treatment site may be current controlled, voltage controlled, power controlled and/or temperature controlled. The electrical signal comprises a continuous charge-balanced waveform or impulse, or additive combination thereof. Alternatively, the electrical signal comprises a not charged-balanced waveform or impulse, or additive combination thereof.

The strength of the electrical field generated at the target site is greater than 10 kV/m. The electrical stimulation delivered to the treatment site generates or induces an electrical field strength at the target site and/or the one or more electrodes between about 20 kV/m and about 2,000 kV/m. The electrical field generated at the target site ranges between 20 kV/m to 2,000 kV/m at its temporal peak, 25 kV/m to 500 kV/m, or 50 kV/m to 400 kV/m. In a transmucosal application, the electrical stimulation generates or induces an electrical field strength at the target site and/or the electrode preferably between about 20 V/m and about 1,000,000 V/m. The strength of the electrical field varies as a function of distance from the electrode, shape of the electrode, and other factors such as the conductivity of the different tissues near the electrode. Tuning of waveform parameters of the stimulation waveform enables control of the spatiotemporal electrical field within the tissue and at the interface of the electrode with the tissue. Tuning of the waveform parameters of the stimulation waveform also enables control of the spatiotemporal thermal field within the tissue and at the interface of the electrode with the tissue. The spatiotemporal variations and levels of the electrical field and the thermal field are important factors in producing the desired selective, reversible inhibition of pain in the target neural structures. Additionally, a cooling mechanism, as will be discussed in detail below, implemented in concert with the waveform and other aspects of the stimulation such as the electrode, enables control and reduction of the spatiotemporal thermal field independent or semi-independent from the electrical field. Separation of these two important variables ultimately enables delivery of a selective, reversible, and tunable treatment that is nondamaging to the neural tissue.

In addition to selectively treating different fiber types, the parameters of the electrical stimulation and the induced electric field and the parameters of the electrical waveform can also be adjusted to preferentially modulate nerve signal transmission within a desired region of the nervous structure, where the desired region of the nervous structure is a portion of the nervous structure less than its complete cross-section.

The electrical stimulation can also be adjusted to reduce onset response (e.g., a pulsing sensation at the nervous structure, motor response in a muscle adjacent the target nerve, such as a muscle spasm or twitching, and activation of the nervous structure during delivery of the electrical stimulation to the nervous structure.

Example Cooling Mechanism

It is also contemplated that the stimulation device 100 can include a cooling mechanism to prevent damage to the patient's tissue during delivery of the electrical stimulation. The cooling mechanism can be integral with the electrode 120 and/or a separate component from the electrode 120 that can is coupled to the electrode or positioned at the treatment site separate from the electrode 120. The cooling mechanism can be controlled by the controller 130 or include a separate controller for directing its operation. The cooling mechanism is used to provide a cooling effect at the contact surface of the stimulation device 100 and/or contact surface of the electrode 120 and/or within the tissue near the treatment site.

It is appreciated by those skilled in the art that delivery of electrical stimulation waveforms to tissue can result in heating of the tissue adjacent the delivery electrode 120. When heating of the tissue is excessive, thermal damage to the tissue can be created. One objective of the present invention is to produce selective and reversible inhibition of pain perception while preserving other sensory and motor function, and proprioception. Thermal lesions of tissue have been deliberately used to ablate or inhibit transmission of nerve action potentials, however, these approaches do not preserve sensory and motor function and proprioception. Additionally, cooling of tissue has been used with thermal ablations, for example with cooled radiofrequency ablations, to enable an increase in power dissipation in the tissue, allowing for an increase in the power of an RF waveform and creation of a larger thermal lesion. However, these cooled RF approaches aim to raise the tissue temperature to at least 60-90° C. in order to create a thermal lesion in the tissue. In contrast, the present disclosure contemplates use of a cooling mechanism that will preserve tissue below thermal damage levels while enabling delivery of an electrical signal that can result in inhibition of pain while preserving sensory, motor and proprioceptive function in the nervous structure.

The cooling mechanism creates a cooling effect that prevents damage to the patient's tissue when the electrical stimulation is delivered by preserving temperatures of the patient's tissue below a destructive tissue temperature, e.g., below temperatures likely to cause thermal damage to the tissue (for example avoiding temperatures that rise above 42-45° C. for a period of multiple seconds). The cooling mechanism maintains the temperature of the contact surface of the stimulation device 100 and/or electrode 120 below a destructive tissue temperature in response to feedback information received from the electrode 120 and/or input from the patient and/or operator. The feedback information includes the measured temperature data received from a temperature sensor 210 coupled to the stimulation device 100. The temperature sensor 210 can measure the temperature of the contact surface of the electrode 120 and/or the temperature of the patient's tissue adjacent the contact surface of the electrode 120. The temperature sensor 210 is electrically coupled to the controller 130 and provides feedback information regarding the measured temperature. As described below, in response to the temperature feedback information, operation of the cooling mechanism and/or parameters of the electrical stimulation can be adjusted to control the temperature at the contact surface of the electrode 120, thereby reducing the temperature of the adjacent patient tissue.

In one example, the cooling mechanism may comprise a pump which circulates a cooling medium such as a gas or pressurized fluid (e.g., carbon dioxide, nitrogen, water, propylene glycol, ethylene glycol, salt water, or mixtures thereof) through the electrode 120 via the conduits 160 provided in the leads (L) (see FIGS. 3A-3E). The circulated gas/fluid serves to remove heat from the electrode 120, tissue of the treatment site and the neighboring tissues. This gas/fluid may be delivered at room temperature or may be cooled below room temperature by use of an incorporated gas/fluid cooling unit or by use of ice or other cooling mechanisms. The cooling of the gas/fluid may be performed before treatment and during treatment. A thermally insulating coating or sheath may also be incorporated around the leads (L) to prevent heating of the cooling medium by heat transfer to the ambient environment.

In another example, the cooling mechanism includes a heat transfer material provided in contact with the tissue of the treatment site and/or the electrode 120. The heat transfer material can be disposed within the electrode 120/leads (L), on an exterior surface of the electrode 120, and/or on an introducer. The heat transfer material acts as a heat sink removing heat from the electrode 120, the tissue of the treatment site and the neighboring tissue. The heat transfer material can include a thermally conductive material (e.g., metal, ceramic material, conductive polymer) and/or one or more Peltier circuits. The thermally conductive material can also include a phase change material that can change phase at a temperature between about 40° C. and 100° C. An example phase change material includes a paraffin wax provided in a pathway that extends from the electrode 120/treatment site to the ambient air. Heat exchange between the paraffin wax and the ambient air serves to remove heat from the electrode 120/treatment site and the neighboring tissues. Additional exemplary cooling mechanisms are described in U.S. Application No. 62/403,876, filed Oct. 4, 2016, entitled "Cooled RF Probes," incorporated herein by reference.

In addition to preventing damage to tissue, the cooling mechanism enables selective inhibition of pain. For example, non-selective inhibition of pain, where motor or non-painful sensory or proprioceptive function is also inhibited, can be observed when temperatures are not preserved below a desired threshold (such as 42-45° C. for a period of multiple seconds). Preservation of the target tissue below such a thermal threshold by use of a cooling mechanism enables selective inhibition of pain without modulating or inhibiting other functions of the nervous structure. Thus, the temperature of the electrode and the tissue is an important parameter that can be tuned by means of the cooling mechanism to enable selectivity of inhibition of pain.

Use of the cooling mechanism also enables treatment of nervous structures of various shapes, sizes, and compositions. For example, the size of the spatial electric field generated by the electrical waveform in the tissue may need to be increased in order to encompass larger nervous structures such as large peripheral nerves, cranial nerves, ganglia, autonomic nerves, portions of the spinal cord, and plexuses. One method for increasing the size of the spatial electric field is to increase the amplitude of the electrical waveform. Use of the cooling mechanism enables an electrical waveform to be delivered with higher amplitude while maintaining the tissue at thermal levels that avoid thermal damage. For example, when peripheral nerves with a diameter greater than 2.5 mm are treated by the stimulation device 100, use of the cooling mechanism enables the electrical waveform parameters, including the amplitude, to be adjusted to levels high enough to treat the larger nerve target without producing thermal damage to the nervous structure. In another example, the nervous structure, such as the spinal cord or ganglia (e.g., gasserian ganglion, sphenopalatine ganglion (SPG)), may be composed of and surrounded by various tissues with different thermal and electrical conductivities. In this case, the cooling mechanism enables delivery of a therapeutic waveform which produces the desired selective and reversible inhibition of pain within a desired region of the nervous structure while preventing thermal damage at sites (including the nervous structure and its surrounding tissue) which are more prone to heating.

Furthermore, use of the cooling mechanism enables tuning of the spatial field of tissue treated by the electrical signal to allow modulation of nerve signal transmission within a desired region of the nervous structure, where the desired region of the nervous structure is a portion of the nervous structure less than its complete cross-section. Cooling may be applied to tissues near the electrode 120 or to tissues neighboring the target treatment site to prevent tissue temperatures from exceeding a desired threshold level. For example, stimulation delivered via an electrode without cooling may produce a thermal field within the tissue which would be thermally damaging at some locations in the tissue. Use and placement of the cooling mechanism at locations which are anticipated to produce thermal damage to tissue enables non-damaging treatment and tuning of the spatial field of tissue treated by the electrical signal. In another example, thermal impulses in the tissue may be produced during short (e.g. less than a second) periods of time. The cooling mechanism enables reduction of these thermal impulses below a threshold level at specific locations in the tissue to enable tuning of the spatial field of tissue treated by the electrical signal. In another example, cooling and electrical waveform parameters may be adjusted concurrently to allow for treatment of a nervous structure (either treatment of a portion of the nervous structure less than its complete cross section or treatment of an entire cross section of the nervous structure) without producing thermal damage.

Example Electrode

FIGS. 3A-3E provide schematic representations of various example electrodes 120 for delivering electrical stimulation to the target nervous structure. The electrodes 120 in FIGS. 3A-3E are in the form of a percutaneous electrode(s) configured for placement nearby (e.g., the electrode is within about 1 cm, within about 5, or less than 2 mm of the nervous system structure, without contacting the nervous system structure), around, and/or contacting a target nerve. The example electrodes are illustrated in FIGS. 3A-3E in a side perspective view. Exemplary percutaneous electrodes are also described in U.S. patent application Ser. No. 15/501, 450, filed Feb. 3, 2017, titled "Selective Nerve Fiber Block Method and System," incorporated herein by reference.

Figure 3B:
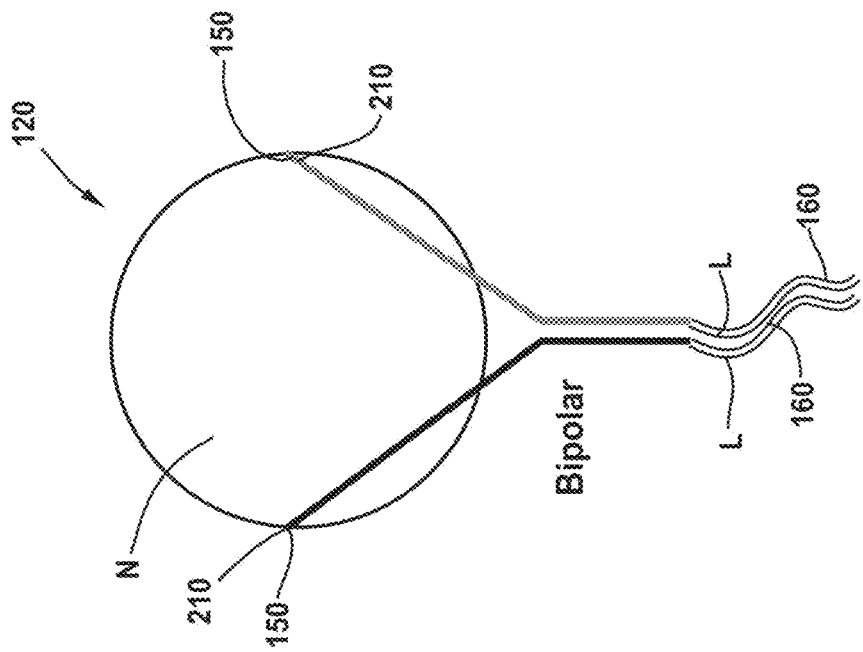
FIGS. 3A-3F are schematic representations of example percutaneous electrodes.
Figure 3A:
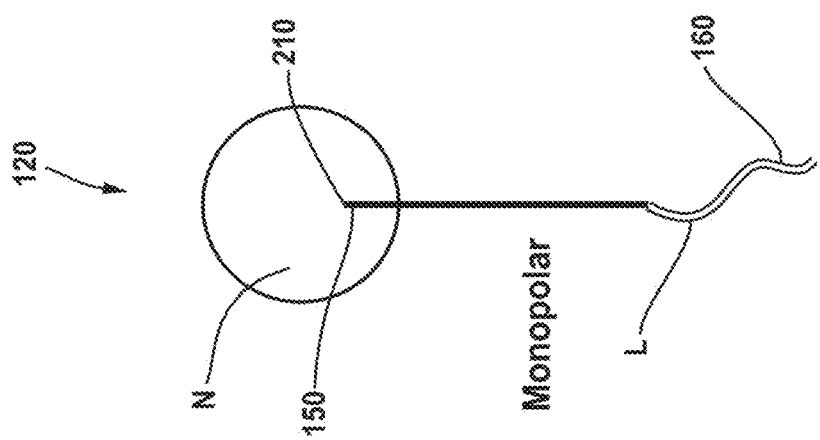
Figure 3E:
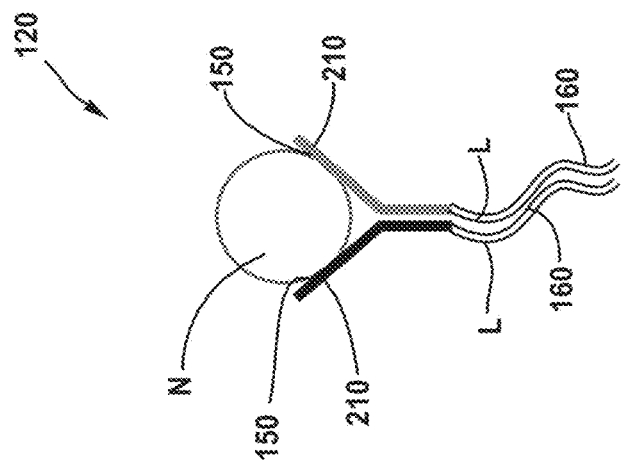
Figure 3D:
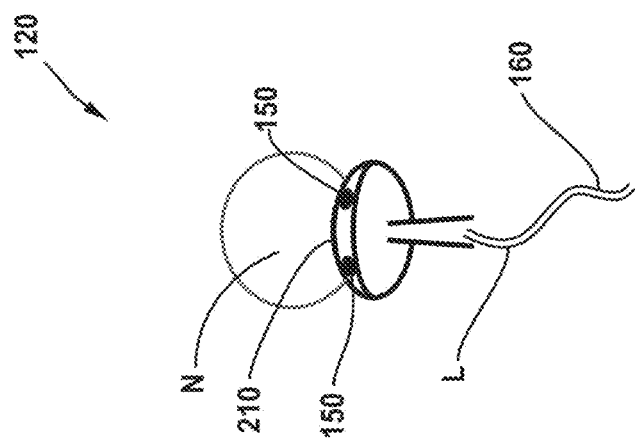
Figure 3C:
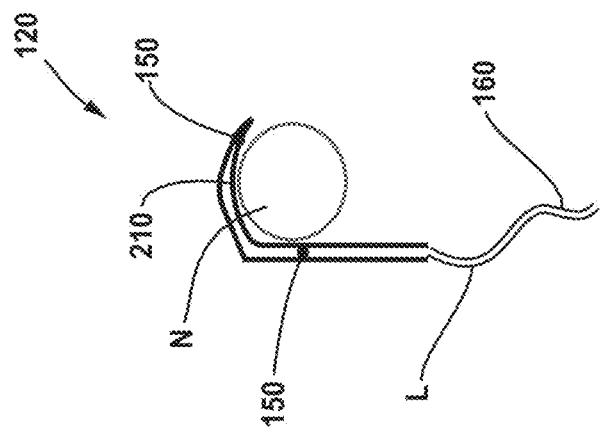
Figure 3F:
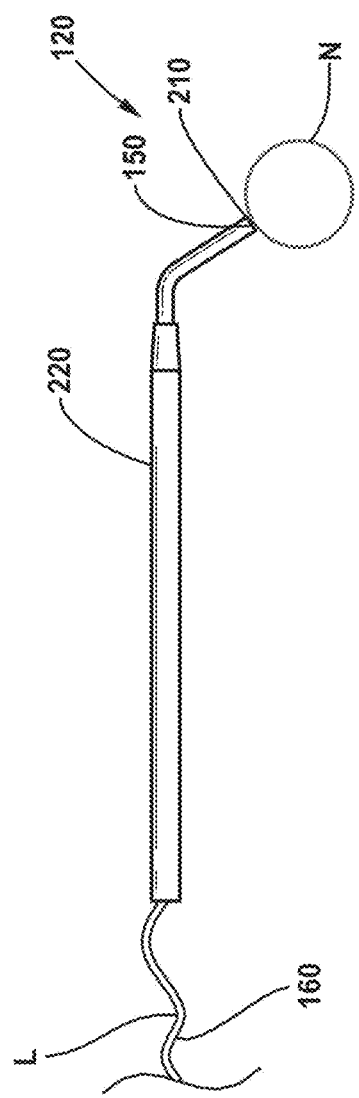

Each electrode used in a bipolar or multi-polar fashion has at least one anode region and at least one cathode region placed nearby/contacting the target nerve "N". The monopolar electrode 120 illustrated in FIG. 3A can include a cathode located nearby a nerve, and a return electrode (e.g., anode) positioned some distance away (e.g., in the form of a patch electrode on the surface of the skin). Bipolar and multipolar electrode configurations, as illustrated in FIG. 3B, have at least one cathode and one anode in the vicinity of the nerve. The electrode shape and size, and inter-electrode spacing are specific to contouring the electrical field and thermal fields surrounding and penetrating the nerve, to enable selective and reversible modulation of the target nervous structure. FIG. 3C provides another example percutaneous electrode 120 having a hook or J-shape. As illustrated in FIG. 3C, the electrode 120 is sized and configured to conform to the target neural structure laterally within the convex portion of the hook shape such that, once positioned, the neural structure is retained near the electrode 120 and contact between the neural structure and the electrode contacts 150 is ensured. Such an electrode may be designed to be inserted via an introducer and in such a way that the hook/J-shaped portion of the end of the electrode is bent within the introducer providing a reduced profile. Upon exit from the introducer, the bent portion of the electrode 120 expands and curves around the surface of the nervous structure. FIG. 3D illustrates an example electrode 120 where the electrode tip defines a generally hemi-spherical shape and provides a generally uniform nerve contacting surface. The electrode may include an expandable conductive surface that when inserted through a small-diameter introducer is confined/not expanding and provides a reduced profile. Upon exit from the introducer, the expandable conductive surface is expands to conform around the surface (or a portion of the surface) of the target neural structure. FIG. 3E illustrates an example electrode 120 having a V- or U-shape. As illustrated in FIG. 3E, the electrode 120 is sized and configured to be placed such that the target nervous structure is positioned laterally within the convex portion of the V/U-shape. Once located at the treatment site, the nervous structure is positioned within the electrode 120 convex portion of the electrode to maintain contact with the contacts 150 on longitudinally opposite sides of the nervous structure. FIG. 3F illustrates an example electrode 120 for use in treating a nervous structure and any overlying mucosal tissue. Specifically, the electrode of FIG. 3F is suitable for use in delivering electrical stimulation to the gasserian ganglion and/or the sphenopalatine ganglion (SPG). The stimulation device includes an elongated body portion 220 sized and configured to be advanced through the nostril of the patient and along the superior border of the middle nasal turbinate. One or more electrodes 120 are provided at a distal end of the elongated body portion 220. The electrode 120 has a contact surface having a size corresponding to a size of the SPG such that the electrical stimulation provided at the electrode 120 can modulate the entire SPG simultaneously and also provide a uniform pressure on a mucosal layer proximate/overlaying the SPG. In general, the contact area of the electrode 120 would range between 1.57-56 mm$^2$. With width of the contact surface of the electrode 120 ranges between at least 1 mm and 6 mm. In one example, the contact surface of the electrode 120 has an elongated triangular shape, a ball-tipped, or half-ball, or flat circular shape. As described above, the electrode of FIG. 3F is designed to be advanced through the nasal cavity to a position adjacent the sphenopalatine ganglion (SPG). As such, the elongated body portion 220 ranges from 5 cm long to 20 cm long. The elongated body portion 220 has a contour corresponding to a superior border of the middle nasal turbinate. To ease in delivery and position, it is also contemplated that the elongated body portion 220 is composes of a flexible material. Though not illustrated, it is contemplated that the stimulation device 100 and/or electrode 120 can be sized and configured to be placed in the patient's mouth. For example, the electrode 120 can be located on a mouthpiece fitted around the gums and teeth such that the electrode 120 is positioned on the gingival tissue (e.g., on the gum line). The electrode 120 can be located on the mouthpiece so that, when worn, it is located adjacent at least one of a ganglia or a peripheral nerve, including, for example, a lingual nerve, an aleveolar nerve, and a buccal nerve.

The electrode 120 can include one or more contacts 150 for delivering the electrical stimulation to the treatment area/target nervous structure. A contact 150 is defined as a portion of the electrode 120 which is intended to form the interface between the electrode 120 and the tissue at which the electric stimulation is delivered to the tissue (such as to generate an electric field in the tissue). The electrode 120 and contact 150 configuration can be designed to maximize and direct the electric field and flow of current into the target nervous structure, and deliver a therapeutic dose of the electrical stimulation to nerves of various sizes and shapes and compositions, and without unwanted stimulation of nearby tissue, while ensuring reliable placement of the electrode 120 relative to the neural structure for optimum therapeutic effect.

Relevant design factors of the electrode include contact number, size, geometry, orientation, material, electrolytic medium, delivery fashion (e.g., monopolar, bipolar, multi-polar), and return path. Adjustment and tuning of these factors enables the electric field and thermal field to be steered through the appropriate neural structure or portion neural structure to produce selective and reversible inhibition of pain. Additionally, adjustment and tuning of these factors enables the electric field and thermal field to be steered through the appropriate neural structure or portion of the neural structure to allow the therapeutic treatment to be effectively delivered in a single application and to adjust the time-course of reversibility of the treatment effects. Tuning and adjusting these factors also allows for shaping of the electric and thermal fields to treat the entire cross section of large nervous structures such as large peripheral nerves (>2.5 mm diameter), cranial nerves, ganglia, autonomic nerves, plexuses, and the spinal cord, as well as to treat portions of both large and small neural structures. For example, the size and shape of electrical contacts or the number of electrical contacts can be adjusted to optimize surface area contact with a large nerve. Likewise, the size and shape of electrical contacts or the number of electrical contacts can be adjusted to optimize surface area contact/electrical stimulation transmission to a nervous structure underlaying a mucosal tissue. SURFACE AREA The electrode contact number, size, geometry, orientation, material, electrolytic medium, delivery fashion (e.g., monopolar, bipolar, multipolar), and return path can also be adjusted to prevent thermal damage to the tissue. These factors influence the thermal field produced by the electrical waveform, including the occurrence of thermal damage at some locations in the tissue relative to the electrodes, and adjustment of these factors, including adjustment in the context of cooling mechanisms and waveform adjustments, enables avoidance of thermal damage to the tissue.

For example, the electrode 120 is sized and configured to maximize and direct the electrical field created by the electrical stimulation delivered to the target nervous structure. The electrical contact 150 of the electrode can have a surface area ranging from about 1 mm$^2$ to about 100 mm$^2$ to accommodate the sizes of electric and thermal fields that are needed to deliver therapeutic treatment to portions of small and large nervous structures as well as to the entire cross section of small and large nervous structures. Preferably the electrode contact 150 has a surface area ranging from about 2.5 mm$^2$ to 45 mm$^2$. Electrical contacts which are too large may include portions of the contact 150 surface which do not contact the neural structure and, as a result, serves as a shunting pathway through which current may flow. When designing electrodes for therapeutic treatment of a nervous structure, shunting current is often discouraged because it increases the necessary current to be supplied from the controller in order to produce the therapeutic effect. Thus, electrical contact sizes and shapes are optimized based on the desire to target delivery of the therapeutic electric field and thermal field to the nervous structure while maintaining the needed current flow from the controller to produce the therapeutic effects.

In another example, the electrode 120 can include at least two contacts 150 that operate dependently in a multipolar fashion to allow for current-steering and/or current-focusing of the resultant electric field. In another example, the electrode 120 includes at least two contacts 150 (e.g., two contacts 150 on the same electrode 120 or multiple electrodes 120 with their corresponding contacts 150) that operate independently. In this manner, the electrical simulation delivered by each of the electrodes 120 can be interleaved such that the total electrical stimulation delivered to the neural structure is delivered in less (half) the time. Specifically, each of the separate electrodes 120 can deliver an intermittent electrical stimulation signal, where the electrical stimulation of the first electrode is interleaved with the electrical stimulation of the second electrode, e.g., an "on cycle" of the first electrical stimulation delivery occurs during an "off cycle" of the second electrical stimulation and an "on cycle" of the second electrical stimulation delivery occurs during an "off cycle" of the first electrical stimulation.

In another example, the electrode 120 can include multiple electrode contacts 150 that can be selected for steering of the electric and thermal fields by selecting one or more electrode contacts 150 to be used as the anode and one or more other electrode contacts to be used as the cathode. The selection of different electrode contact combinations enables adjustment of the shape and size of the electric field and thermal field. For example, a brief test pulse of electrical stimulation may be delivered via a subset of contacts to determine proximity and coverage of the nerve, and more contacts may be added until sufficient contact with the nerve is verified (for example by monitoring motor output of the leg via movement or electromyography).

Generally speaking, the electrical stimulation may be delivered to the target nervous structure utilizing an electrode 120 that may be in the form of a percutaneous electrode assembly to temporarily and selectively modulate nerve fiber activity in the target nervous structure. For example, the electrode 120 can include an electrode assembly in the form of a paddle, cuff, cylindrical catheter or needle, wire form, or thin probe, configured to be introduced percutaneously through an opening in the patient's skin. In another example, for use in in the treatment of head and face pain (as described in more detail herein), the electrical stimulation may be delivered to the target nervous structure via and electrode 120 placed on a mucosal tissue of a patient, e.g., an electrical probe sized and configured to be advanced transnasally a target site proximate the gasserian ganglion and/or sphenopalatine ganglion (SPG).

Additionally, the electrical stimulation may be delivered to the target nervous structure via an electrode 120 implanted in the patient, for example for the treatment of chronic pain. In this case, the electrode 120 may be surgically implanted, and may be placed in contact or around the neural structure during a surgical procedure or during a minimally-invasive implant procedure. The electrode 120 may be secured to the neural structure and to surrounding tissue using sutures or using anchoring structures built on to the electrode that secure the electrode to neural structures or neighboring tissues.

The lead (L) includes a means for transmitting electrical energy between the electrical stimulation device 100 and the electrode 120, such as via a conductive wire or cable. The lead (L) may be directly attached to the electrode 120 in a permanent fashion or may be attachable and detachable using a conductive connector. In this case, compatible connectors would be present on the electrode 120 and on the lead (L). The lead may be directly attached to the electrical stimulation device 100/signal generator 140 in a permanent fashion or may be attachable and detachable using a conductive connector. In this case, compatible connectors would be present on the electrical stimulation device 100/signal generator 140 and on the lead (L). The lead (L) may also include avenues for transmission of fluid/gas, such as conduits 160 used for transmitting fluid/gas used to cool the electrode(s) 120. Fluid transmission conduits 160 may be connected to the electrode 120 and a cooling device directly or via attachable/detachable connectors. The lead (L) may also be contoured to provide a shape that is optimal for placement of the electrode 120, for example to allow navigation of the electrode into an ideal location near the nervous structure and to navigate around obstacles or tissue presenting a partial barrier between the insertion point and the target neural structure.

The lead (L) and electrode 120 may be placed with the help of lead introducer tools, such as cannulas, guidewires, introducer needles, and trocars. Particularly for percutaneous placement, these lead and electrode introducer tools may be used to navigate through the skin and underlying tissues to a position near the target neural structure. The introducer tool can also be used to allow for introduction/placement of all needed contacts 150 and other electrode components near the target neural structure. The lead (L), electrode, and introducer tools allow for placement of the electrode near both large and small target neural structures, including peripheral nerves, a cranial nerves, ganglia, autonomic nerves, a plexuses, and the spinal cord, and also enable appropriate interfacing between the electrode(s) and these target neural structures, which assists with producing selective and reversible inhibition of pain perception. The lead (L), electrode, and introducer tools also allow placement of the electrode 120 in cases of percutaneous use, for example for acute pain, and for implanted use, for example for chronic pain.

Example Signal Generator

The electrical stimulation device 100 can include a signal generator 140 coupled to the electrode 120 and the controller 130. The signal generator 140 produces the stimulation waveform, including the parameters of the stimulation waveform discussed above. The signal generator 140 includes the necessary software and hardware components to produce the specified stimulation waveform(s) and to allow for modulation of the stimulation waveforms by means of the controller 130. The signal generator 140 also includes the ability to deliver stimulation to the nervous structure via the electrode(s) 120 while electrically isolating the electrode 120 and patient from grounded circuitry and other ground connections, such that the patient is not grounded when the electrode(s) are introduced in the patient's body. This is accomplished, for example, via inductors or via optical isolators. Additionally, the signal generator 140 can include capacitors, inductors, resistors, and other passive circuit components near the output to the electrode 120 which ensure charge balance, reduce DC offset, or otherwise provided the desired regulation of the waveform parameters discussed earlier. Furthermore, feedback monitoring circuitry can be incorporated to collect information regarding the waveform delivered (such as the current, voltage, power) and the temperature (for example as monitored via a temperature monitoring mechanism (e.g., temperature sensor 210) at the electrode 120 or otherwise in the tissue). Parameters of the cooling mechanism such as temperature of the fluid/gas cooling medium, flow rate and pressure of the fluid/gas, the heat transfer rate from the electrode 120 and/or surrounding tissue, etc. may also be gathered.

Example Controller and Power Supply

As described generally above, the controller 130 directs operation of the stimulation device 100/signal generator 140 to provide the electrical stimulation to the target neural structure by means of the electrode 120. The controller 130/signal generator 140 are electrically coupled to a power source 180 that supplies the electrical energy to the stimulation device 100/electrode 120. The power source 180 can include an isolated power supply, such that all the instruments in the system can be powered by an isolated power supply 180 to protect them from ground faults and power spikes carried by the electrical main. The power source 180 can also include one or more batteries, used either for primary or backup power, which would allow the device to be operated without attachment to the electrical main at the facility.

Specifically, the controller 130 directs operation of the signal generator 140 to deliver an electrical stimulation signal to the target nervous structure. The controller 130 may have onboard memory to facilitate high speed data capture, output control, and processing, as well as, independent waveform sample rates and on-line analysis. These components of the controller enable collection of the feedback data needed to understand the waveform delivered via the electrode as well as the parameters of the cooling mechanism and the thermal and electrical state of the tissue. This feedback enables tuning of such treatment parameters in order to provide selective and reversible inhibition of pain.

As illustrated schematically in FIG. 1, the stimulation device can include one or more electrodes 120 connected by to an electrical lead (L) to the controller 130 via the signal generator 140. The controller 130 can include control logic and software designed to deliver the desired electrical stimulation to a patient. The controller 130 can also process analog and digital data, and record waveform data and digital information from the patient monitor system 190 and can generate waveform outputs, analog outputs, and digital outputs simultaneously for real-time control of the electrical stimulation (either real-time automated control, or manual user control). For example, the controller 130 can adjust the electrical stimulation in response to feedback information received from temperature sensors coupled to the electrode 120 and/or the stimulation device 100. For example, the stimulation device 100/electrode 120 can include a thermocouple for measuring the temperature at the contact surface of the stimulation device and/or the electrode contacts, and the patient's tissue adjacent the contact surface of the electrode 120. The temperature sensors are coupled to the controller 130 and provide feedback information regarding a measured temperature at the contact surface of the stimulation device 100 and/or the contact surface of the electrode 120 and/or at other locations in the tissue. The controller 130 or the user can then adjust a parameter of the electrical stimulation in response to the feedback information, the parameters including, for example, a waveform shape, a waveform frequency range, a waveform amplitude range, an electrical field strength generated at the electrode, a waveform DC offset, a waveform duty cycle (e.g., continuous delivery or intermittent delivery) a tissue temperature, a cooling mechanism parameter, and a treatment duration. Additional feedback signals that may be relayed or recorded by the controller or used for feedback control of the electric signal include temperature, contact impedance, the current, voltage, and power of the electric signal, other parameters of the electric signal, information regarding the electric field in the tissue, blood flow, skin conductance, heart rate, muscle activity (such as electromyography), or other physiological signals.

Feedback control of the electrical stimulation is desirable to avoid producing damage in tissue, to tune the sphere of modulation of the electrical stimulation within the target neural structure, and to tune the sphere of modulation of the electrical stimulation to target both small and large nervous structures and a diversity of nervous structures such as peripheral nerves, a cranial nerves, ganglia, autonomic nerves, plexuses, and the spinal cord. Feedback control of the electrical stimulation is also desirable to enable tuning of the time course of reversibility of the inhibition of perception of pain, to tune the selectivity of the inhibition of perception of pain, and to ensure that adequate inhibition of pain is achieved, for example, with a single treatment.

Whether adjusting the electrical stimulation to selectively modulate nerve signal transmission through a select type of nerve fiber and/or through a select region of the nervous structure, the control and/or operation of the controller 130 can be adjusted varying a parameter of the electrical stimulation based on a measured feedback of the inhibition of nerve signal transmission (e.g., confirmation of no or limited nerve signal transmission from/through the target nerve), and/or a measured feedback of the temperature at the treatment site, and/or feedback from the patient regarding pain perception. The controller 130 and the user interface are also used to adjust the parameters of the stimulation waveform and properties of the electrode configurations and the cooling mechanism in response to feedback. Alternatively, a user can manually adjust parameters of the stimulation waveform and properties of the electrode configurations and the cooling mechanism in response to feedback provided via the user interface 170.

Example User Interface

The stimulation device 100 may further include a user interface 170 for receiving input from and providing input to the user (e.g., patient or medical professional). The user may provide input directing operation of the stimulation device 100 including modifications to the electrical signal. The user interface 170 can further include a display providing information to the user regarding the stimulation device 100. For example, the display can provide information regarding a status of the stimulation device 100, e.g., on/off, signal delivery mode, parameter date regarding the electrical signal, etc. The user interface 170 may be integral to the stimulation device 100. It is also contemplated that the user interface 170 may be incorporated into a remote device that is electrically (wire or wireless) coupled to the stimulation device. For example, the user interface 170 may be provided on an external tablet computer or phone. The user interface 170 may be used to allow the user to actively control parameters of the electrical stimulation (in real time) in response to feedback information from the controller 130.

The system can also include a patient monitoring system 190. The patient monitoring system 190 may be used in conjunction with the stimulation device and the user interface 170. The patient monitoring system 190 acquires, amplifies and filters physiological signals, and outputs them to the controller 130 and/or the user interface 170 for feedback. The monitoring system can include a temperature sensor coupled to an outer surface of the patient's skin for measuring changes in the patient's surface body temperature, a blood flow meter coupled to the patient's skin or inserted through the patient's skin, a skin conductance meter coupled to the patient's skin, a heart-rate monitor to collect electrocardiogram signals corresponding to the patient's heart rate, and a muscle activity monitor to collect electromyography signals. A heart-rate monitor may include separate electrocardiogram (ECG) electrodes coupled with an alternating current (AC) amplifier. A muscle activity monitor may include separate EMG electrodes coupled with an AC amplifier. Other types of transducers may also be used. As described, all physiological signals obtained with the patient monitoring system are passed through a signal amplifier/conditioner. The parameters of the electrical stimulation can be adjusted in response to the feedback information received at the patient monitoring system 190 by either the controller 130 or user. For example, at least one parameter of the electrical signal can be adjusted by the controller 130 in response to feedback information received from the temperature sensor, an impedance meter, the blood flow meter, the skin conductance meter, the heart rate monitor, and the muscle activity monitor. Information regarding the stimulation waveform and parameters as well as the electrical the thermal properties of the tissue, the electrode, and the cooling mechanism can also be provided via the user interface 170 and used to adjust at least one parameter of the electrical stimulation or the cooling mechanism or the electrode configuration. The adjusted parameter of the electrical signal can include, for example, a waveform shape, a waveform frequency range, an waveform amplitude range, an electrical field strength at the electrode, a waveform DC offset, a waveform duty cycle (e.g., continuous delivery, intermittent delivery), a tissue temperature, a cooling mechanism parameter, and a treatment duration. Additionally, the electrode configuration (e.g. bipolar, multipolar, monopolar, interleaved, etc.) can also be adjusted in response to feedback information.

Example Method

The present disclosure encompasses a method for selectively and reversibly modulating targeted neural- and non-neural tissue of a nervous structure with a single application of electrical energy to inhibit pain perception by a patient. The method of practicing the present invention begins with positioning the patient in a comfortable position. A heart rate monitor (ECG), a muscle activity monitor (EMG), or any other monitor may be utilized to measure the patient's response to the electrical stimulation signal. The patient may be monitored for a period of time to determine a baseline status before the application of the electrical stimulation signal.

Next the targeted nervous structure can be identified and located. If the electrical signal is to be delivered transcutaneously, the targeted nervous structure may be located utilizing a stimulation device such as a nerve locator (e.g., Ambu® Ministim® nerve stimulator and locator), utilizing the electrode 120. The nerve can also be located by passing low-levels of stimulation energy signal through the stimulation device. A stimulus-elicited muscle twitch in a distal muscle group with low stimulation amplitudes (single pulse) will indicate that the stimulation point is close enough for modulating nerve signal transmission.

The electrical stimulation device 100 is then positioned at the treatment site proximate the targeted neural- and non-neural tissue of the nervous structure. Electrode(s) 120 can be positioned near the nervous structure in a percutaneous or transnasal fashion, or by open incision and implantation.

Figure 5:
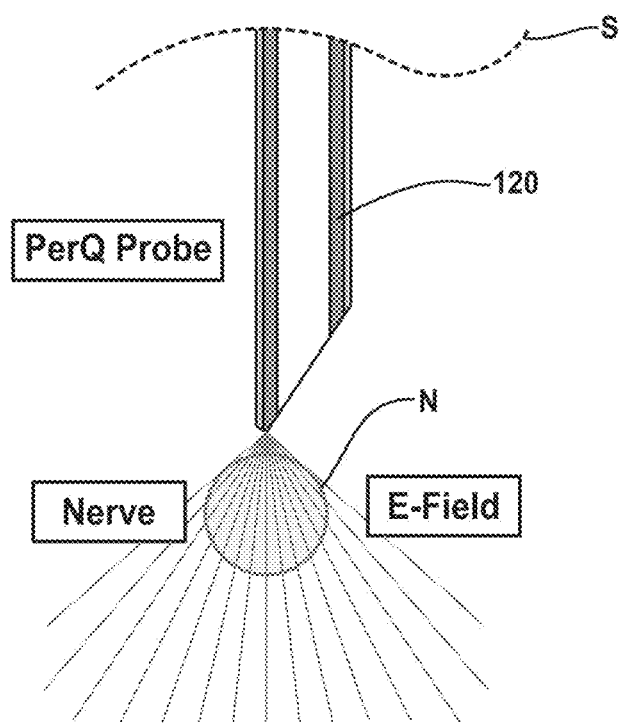
FIG. 5 is a schematic representation of positioning an electrode percutaneously and delivering and electrical stimulation to a target nervous structure.

For example, electrodes 120 can be positioned percutaneously adjacent the nervous structure through an opening in the patient's skin (S) (see e.g., FIG. 5). The (internal) electrodes 120/leads (L) are attached to an external stimulation device/signal generator 140, or can be fixed to a handheld stimulation device. Placement of the electrodes 120 percutaneously may include penetration of the skin and navigation of the electrode 120 and/or lead (L) under imaging guidance (such as with ultrasound) to a location proximate the target neural structure. Additional positioning tools may be used, such as cannulas, guidewires, introducer needles, and trocars to enable navigation of the tissues and eventual placement of the electrode proximate the target neural structure.

Positioning the electrode 120 near the nervous structure may including delivering an initial electrical stimulation to the treatment site via the electrode 120 and measuring the voltage and/or the current at the electrode 120. Based on the measured voltage and/or current, the position of the electrode 120 at the treatment site (near the target nervous structure) is adjusted. Further initial electrical simulation signals are delivered to the treatment site and the position of the electrode 120 is adjusted, iteratively until the measured voltage and/or current corresponds to a threshold voltage and/or threshold current.

Where the electrical signal is delivered percutaneously, the method may further include positioning one or more return electrodes on the outer surface of the patient's skin. Each anode desirably has a skin contacting surface such that the skin contacting surface of the anode has at least the same (or greater) surface area as the contacting surface of the stimulating electrode. One or more return electrode may be positioned on the skin a distance away from one or more stimulating electrodes sufficient to avoid shunting.

The method of practicing the present invention may further include the use of coupling media such as, for example, an electrically conductive liquid, gel or paste that may be applied to the skin in the case of return electrode or disposed within a sheath around the electrode 120 or at the tip of the electrode 120 in the case of the percutaneous placed electrode 120 in order to maximize and direct the electric field, deliver the therapeutic dose of stimulation energy to small and large nerves, and ensure reliable electrode/nerve placement for optimum therapeutic effect. Alternatively and/or additionally, one or more skin moisturizers, humectants, exfoliators or the like may be applied to the skin for the purpose of enhancing the conductivity of the skin and/or lowering impedance of the skin. Example conductive pastes include Ten20™ conductive paste from Weaver and Company, Aurora, Colo., and ELEFIX Conductive Paste from Nihon Kohden with offices at Foothill Ranch, Calif. Examples of conductive gels include Spectra 360 Electrode Gel from Parker Laboratories, Inc., Fairfield, N.J., or Electro-Gel from Electro-Cap International, Inc., Eaton, Ohio. An example exfoliator that can be used to prepare skin prior to application of transcutaneous electrodes is Nuprep skin prep gel from Weaver and company, Aurora, Colo.

In a further example, the electrodes can be implanted within the patient adjacent the treatment site and proximate the target neural structure. The electrodes and the stimulation device can be implanted at or near the target neural structure. In another example the electrodes can be implanted at the treatment site with the leads extending through the patient's skin to the stimulation device. It is also contemplated that the electrodes can be implanted at the treatment site and can be wirelessly activated through the patient's skin. It is also contemplated that a wireless receiver module can be implanted and used to receive input wirelessly from the controller 130, and then communicate with the electrode via lead wires.

Figures 6A, 6B:
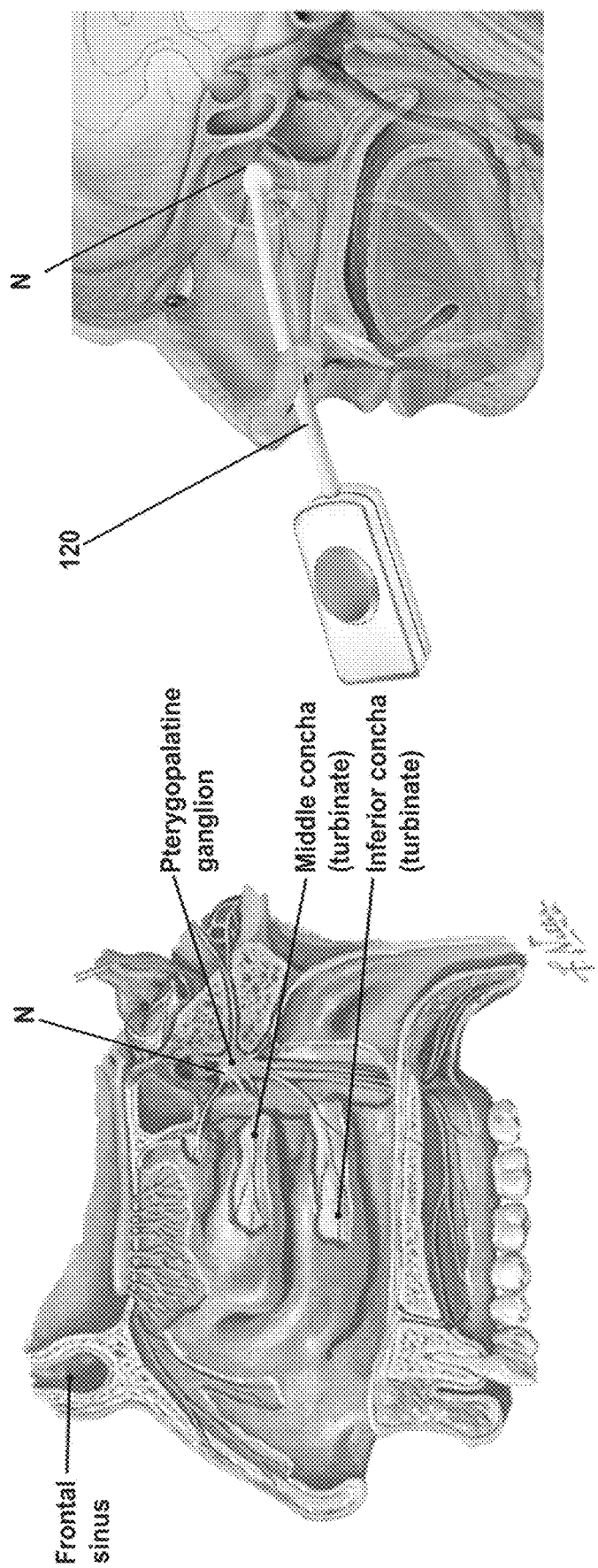
FIGS. 6A and 6B are schematic representations of positioning an electrode and delivering an electrical stimulation the sphenopalatine ganglion.

An additional example is placement of the electrode 120 (e.g. FIG. 3F) in a nasal turbinate via a transnasal approach for transmucosal delivery of the electrical signal to the gasserian ganglion and/or sphenopalatine ganglion (SPG). For example, the electrode 120 and lead may be inserted into the patient's nose and placed in a nasal turbinate and held securely in position during delivery of the electrical signal (see e.g., FIGS. 6A and 6B). A method may be used in which the patient's sneeze reflex is suppressed, for example, using chemical block or electrical nerve block or by intentionally evoking a sneeze reflex and then placing the lead and electrode immediately after the sneeze before the patient is able to generate a second sneeze reflex. The intentional initial sneeze reflex may be triggered by the lead and/or electrode or by a separate probe inserted into the nose. It is also contemplated that the electrode 120 can be positioned adjacent the gasserian ganglion and/or sphenopalatine ganglion (SPG) via a percutaneous approach. Whether via a transnasal or percutaneous approach, the position of the SPG may be initially located using, for example, magnetic resonance imaging (MRI), fluoroscopy, and ultrasound imaging.

After electrodes 120 are placed, traditional electrical stimulation can be delivered through the electrodes 120 to assure sufficient tissue/nerve proximity, and impedance measurements can be collected and used similarly. The stimulation device can them be programed to optimize electrode contact selection, return electrode selection and stimulation parameters, as discussed above. It is contemplated that selection of optimal stimulation parameters can include delivery of different candidate waveforms with different parameter configurations until a suitable outcome is achieved. It is further contemplated that selection of optimal electrode contact 150 configurations and return electrode configurations can include delivery of electric signals via different configurations of electrode contacts 150 and return electrodes until a suitable outcome is achieved. These optimizations may be performed manually by the user or may be delivered by the controller in closed-loop as part of an algorithmic iterative search or a pre-programmed search. If desired, a chemical nerve block agent can also be delivered through the electrode lead prior to delivering the electrical signal. The chemical nerve block can help to mitigate onset response and improve patient comfort.

The stimulation electrical signal can then be delivered to the treatment site proximate targeted nervous structure via the electrode(s) using one or more of the stimulation parameters discussed above. The controller 130, receiving a supply of electrical energy from a power source 180 can direct operation of the stimulation device to provide an electrical signal sufficient to selectively modulate the targeted neural- and non-neural tissue inhibiting the patient's perception of pain while also preserving other sensory and motor function, and proprioception. The user may also control the parameters of the electrical signal in real time in response to feedback provided via the controller 130 to the user interface 170. A single application of the electrical signal to the treatment site can selectively modulate the targeted neural- and non-neural tissue and provide subsequent inhibition of perception of pain, for a period of about 1 day to about 30 days.

Where the electrode comprises at least two electrodes that operate independently, it is contemplated that a first electrical simulation signal may be delivered via the first electrode and a second electrical stimulation signal via the second electrode. The first and second electrical stimulation signals can be intermittently outputted, where the first electrical stimulation is interleaved with respect to the second electrical stimulation. In this configuration, the on cycle of the first electrical stimulation occurs during an off cycle of the second electrical stimulation. Similarly, the on cycle of the second electrical stimulation occurs during an off cycle of the first electrical stimulation.

The perception of pain by the patient is inhibited as the application of the electrical signal to the treatment site selectively modulates the targeted neural- and non-neural tissue modulating the nerve signal transmission through nerve fibers that are responsible for the transmission of pain. Meanwhile, nerve signal transmission through nerve fibers responsible for other sensory and motor function, and proprioception is preserved. The preserved "other" sensory function includes, for example, touch, vision, audition, gustation, olfaction, and balance. Application of the electrical signal can also inhibit and/or disrupt nerve signal transmission through nerve fibers responsible for transmitting signals related to thermoreception, autonomic effector activity and visceral function.

In its simplest form, the method may rely on a patient's feedback regarding their perception of pain after delivery of nerve blocking stimulation signal to assess the effectiveness of the temporary and selective nerve modulation. Alternatively and/or additionally, the method may rely on feedback collected by a recording electrode, such as an ECG, galvanic skin response, blood flow meter, skin or body temperature, and/or electromyogram signals to assess the effectiveness of the temporary and selective nerve modulation, since the stimulation may occur before, during, or immediately after a surgical procedure when the patient is not able to provide feedback.

The target nervous structure can comprise a peripheral nerve (large or small), a cranial nerve, a ganglion, an autonomic nerve, a plexus, and a spinal cord. Target neural structures can include a mixture of motor, sensory and/or autonomic neurons, or may include a single type of neural activity (such as motor only, sensory only, autonomic only). Target ganglia can include a dorsal root ganglia, a sympathetic ganglia, a parasympathetic ganglia, a sphenopalatine ganglion, a gasserian ganglion, a plexus, and/or the spinal cord. In one example, the target nervous structure comprises a large peripheral nerve (such as greater than about 2.5 mm) and the electrodes deliver an electrical signal to the nerve that selectively and reversibly inhibits nerve signal activity associated with pain for a period of days to weeks, with preservation of nerve signaling associated with motor function, non-painful sensation, and proprioception. For example, the electrodes 120 can deliver an electrical signal that selectively and reversibly inhibits nerve signal activity in smaller diameter nerve fibers associated with sensory (pain) function for a period of days-to-weeks, with minimal or no change in the functionality of the larger myelinated fibers that are associated with motor function, non-painful sensation, and proprioception. In one example, the application of the electrical signal to the neural- and non-neural tissues of the targeted nervous structure inhibits and/or disrupts nerve signal transmission through at least one of a myelinated Aδ fiber and/or an unmyelinated C fiber provided in the nerve, wherein the electrical signal preserves nerve signal transmission through at least one of the Aβ and Aα fibers, and/or motor fibers. In a further example, various parameters of the electrical signal can be adjusted to selectively inhibit at least one of the myelinated Aδ fibers or the unmyelinated C fibers, e.g., inhibit nerve signal transmission through the myelinated Aδ fibers while preserving nerve signal transmission through the unmyelinated C fibers, and vise-a-versa. In a further example, various parameters of the electrical signal can be adjusted to differentially inhibit nerve signal transmission/function of the myelinated Aδ fibers, such that the myelinated Aδ fibers have a larger percentage of fibers inhibited than the unmyelinated C fibers. Likewise, various parameters of the electrical signal can be adjusted to differentially inhibit nerve signal transmission/function of the unmyelinated C fibers, such that the unmyelinated C fibers have a larger percentage of fibers inhibited than the myelinated Aδ fibers.

In another example, the application of the electrical signal to the neural- and non-neural tissues of the targeted nervous structure modulates neural or non-neural tissue function in a way the results in downstream or secondary effects that result in the inhibition of pain, while preserving motor, non-painful sensory, and proprioceptive activity. For example, various parameter of the electrical signal can be adjusted to selectively modulate function which results in reduction of pain that originated from activity in myelinated Aδ fibers and/or unmyelinated C fibers, while preserving motor, non-painful sensory, and proprioceptive function, such as that transmitted by Aβ and Aα fibers, and/or motor fibers. In a further example, various parameters of the electrical signal can be adjusted to selectively modulate function which results in reduction of pain that originated from activity in myelinated Aδ fibers or the unmyelinated C fibers, e.g., inhibit pain that originated from activity in myelinated Aδ fibers while preserving pain that originated from activity in unmyelinated C fibers, and vise-a-versa. In a further example, various parameters of the electrical signal can be adjusted to differentially modulate function which results in reduction of pain that originated from activity in myelinated Aδ fibers, such that the pain originating from activity in myelinated Aδ fibers has a larger inhibition than the pain originating from activity in unmyelinated C fibers. Likewise, various parameters of the electrical signal can be adjusted to differentially modulate function which results in reduction of pain that originated from activity in unmyelinated C fibers, such that the pain originating from activity in unmyelinated C fibers has a larger inhibition than the pain originating from activity in myelinated Aδ fibers.

In another example, certain parameters of the electrical signal can be adjusted to preferentially modulate nerve signal transmission/function within a desired region of the nervous structure. Generally, the desired region is that portion of the nervous structure including the sensory components responsible for transmitting a sense of pain. For example, with respect to the femoral nerve, topography of the femoral nerve indicates that portions of sensory components innervating the knee are collected together in a region of the nerve cross-section. Accordingly, it is contemplated that the electrical signal can be adjusted to preferentially modulate nerve signal transmission through the portion of the nerve cross-section corresponding to these target sensory components.

The various, modifiable, wherein the parameters of the electrical signal include, for example, a waveform, a frequency, an amplitude, an intensity, an electrical field strength, a waveform offset (DC offset), a continuous delivery, and/or intermittent delivery through the electrode 120.

The disclosed method encompasses inhibiting the perception of pain associated with acute pain (including surgical pain, post-surgical pain, trauma pain), neuropathic pain, chronic pain, and head-and-face pain. Where the pain is acute pain, the method for selectively and reversibly modulating targeted neural- and non-neural tissue to inhibit the perception of pain may include applying the electrical signal immediately before the surgical procedure. The electrical signal can also be applied intraoperatively and/or immediately following a surgical procedure to inhibit the perception of pain associated with the surgical procedure and recovery. Where the pain is neuropathic pain or chronic pain, the method for modulating the neural- and non-neural tissue of the target nervous structure may include the user (such as a physician or a patient) applying the electrical signal as part of a pre-determined schedule for preventative care, and/or as needed by the patient to provide an on-demand bolus of therapeutic treatment/pain relief.

The method for selectively and reversibly modulating targeted neural- and non-neural tissue to inhibit the perception of pain may further include measuring, at a temperature sensor 210, the temperature the contact surface of the stimulation device 100 (e.g., electrode 120 contact surface) and/or the temperature of the patient's tissue adjacent the stimulation device contact surface during delivery of the electrical signal. The feedback information regarding the measured temperature is provided to the stimulation device. If the feedback information indicates that the temperature of the contact surface of the stimulation device is above a device threshold temperature and/or if the temperature of the patient's tissue is above a tissue threshold temperature, the stimulation device/controller or the user can adjust the operation of the stimulation device and the parameters of the electrical signal and/or a cooling mechanism to produce a cooling effect and reduce the temperature at the contact surface and tissue. Reducing the temperature of the contact surface and/or the patient's tissue prevents damage to the patient's tissue. In some examples, the system may include a cooling mechanism coupled to and/or integrated into the stimulation device 100 and/or electrodes 120. If the feedback information indicate that the temperature of the contact surface of the stimulation device 100 is above a device threshold temperature and/or if the temperature of the patient's tissue is above a tissue threshold temperature, the stimulation device 100/controller 130 and/or the user, may activate and control operation of the cooling mechanism to cool the contact surface of the stimulation device 100/electrode 120 where cooling the contact surface prevents damage to the patient's tissue when the electrical signal is delivered by preserving temperatures of the patient's tissue below a tissue threshold temperature. Likewise, the stimulation device 100/controller 130 and/or the user, may activate and control operation of the cooling mechanism to maintain the temperature of the contact surface of the stimulation device 100/electrode 120 below a threshold temperature in response to feedback information regarding the measured temperature received from the temperature sensor 210.

After the electrical signal has been delivered, and the perception of pain has been inhibited while preserving other sensory and motor function, and proprioception, the percutaneous and/or transcutaneous electrodes 120 can be removed. Meanwhile, implanted electrodes 120 (if any) can remain inside the body for further usage and ongoing treatment.

Example 1

In this example, able-bodied subjects were recruited from the community and consented for the study using IRB-approved consent forms. High-dose opioid users were excluded from the study. Two types of sensory assessment were performed at multiple time-points in each subject: 1) mechanical vibration testing to assess the subject's sensitivity to non-painful touch sensation, and 2) pain-evoking electrical stimulation testing to assess the subject's sensitivity to evoked pain. At the beginning of the first session, mechanical vibration testing and pain-evoking electrical stimulation assessments were performed on each leg. These were referred to as the baseline assessments. The subject then received treatment using the electrical stimulation waveform via a percutaneously-placed electrode on the left leg. After the treatment, the mechanical and vibration testing was again assessed on each leg. Subjects returned in subsequent visits for mechanical vibration testing and pain-evoking electrical stimulation testing.

Mechanical vibration testing: Subjects donned scrubs and were seated in a comfortable chair. The right leg was secured in a straight position to a stand with foam padding to restrict movement. A vibration device was placed in contact with the skin within the saphenous nerve distribution. Vibration trials were then performed in which a series of two epochs were provided to the subject, one including a vibration via the vibration device and the other not including a vibration. For each trial, the selection of which epoch in which vibration was delivered was determined randomly and the subject was requested to indicate verbally which epoch was the epoch during which he or she believed the vibration had been delivered. If the subject selected the correct epoch, a duplicate trial was delivered until successful selection had been made for three sequential trials, after which the vibration amplitude was decreased for the next trial. If the subject selected the incorrect epoch, the next trial was delivered at a higher amplitude of stimulation. In this fashion the threshold amplitude was identified based on the combined performance from 3 sets of 50 trials on each leg. The threshold amplitude was identified for each leg in each session.

Pain-evoking electrical stimulation testing: Electrical stimulation was delivered via sticky surface electrodes placed over the saphenous nerve near the medial malleolus. The stimulation duration was 1 ms for single pulses. The amplitude of stimulation was increased gradually until the subject first perceived sensation. The stimulation was then delivered in a train of 9 pulses at 500 Hz and the stimulation amplitude was gradually increased until the subject perceived a transition from non-painful sensation to painful sensation. The pain threshold was identified via both ascending and descending limit tests and the average pain threshold for that session was documented. This threshold was identified for each leg in each session.

Electrical stimulation treatment: Electrical stimulation treatment was delivered in a single treatment to each subject in the left leg only. After the baseline mechanical vibration testing and the baseline pain-evoking electrical stimulation testing, the subject was prepared for delivery of the electrical stimulation treatment.

The subject was placed supine on a procedure table and the skin was prepped at a site over the saphenous nerve several centimeters distal and medial to the tibial tuberosity. A surface return electrode was placed on the contralateral leg over the gastrocnemius muscles. Ultrasound was used to identify the saphenous nerve and a radiofrequency probe (22-gauge, 4-mm exposed tip) was inserted through the skin. The position of the radiofrequency probe active tip was manipulated while stimulation (1 ms duration, 2 Hz) was delivered at progressively lower amplitudes. Manipulation of the probe position was performed until a sensory threshold was achieved at less than 0.2 V.

The electrical stimulation treatment was then delivered to the subject at 2 Hz, 20 ms, for 240 s. The amplitude of the stimulation was adjusted in real time to maintain a probe tip temperature of 42° C. After completion of the stimulation the probe was removed and the subject again underwent mechanical vibration testing and pain-evoking electrical stimulation testing, referred to as visit 0.

Subjects returned for follow-up assessment in subsequent visits. Vibration thresholds were plotted over time to assess the effect of the electrical stimulation treatment on touch sensation, such as sensation transmitted via large-diameter myelinated fibers. Pain thresholds were normalized to the baseline level and plotted over time to assess the effect of the electrical stimulation treatment on painful sensation, such as sensation transmitted via small-diameter fibers.

Figure 7:
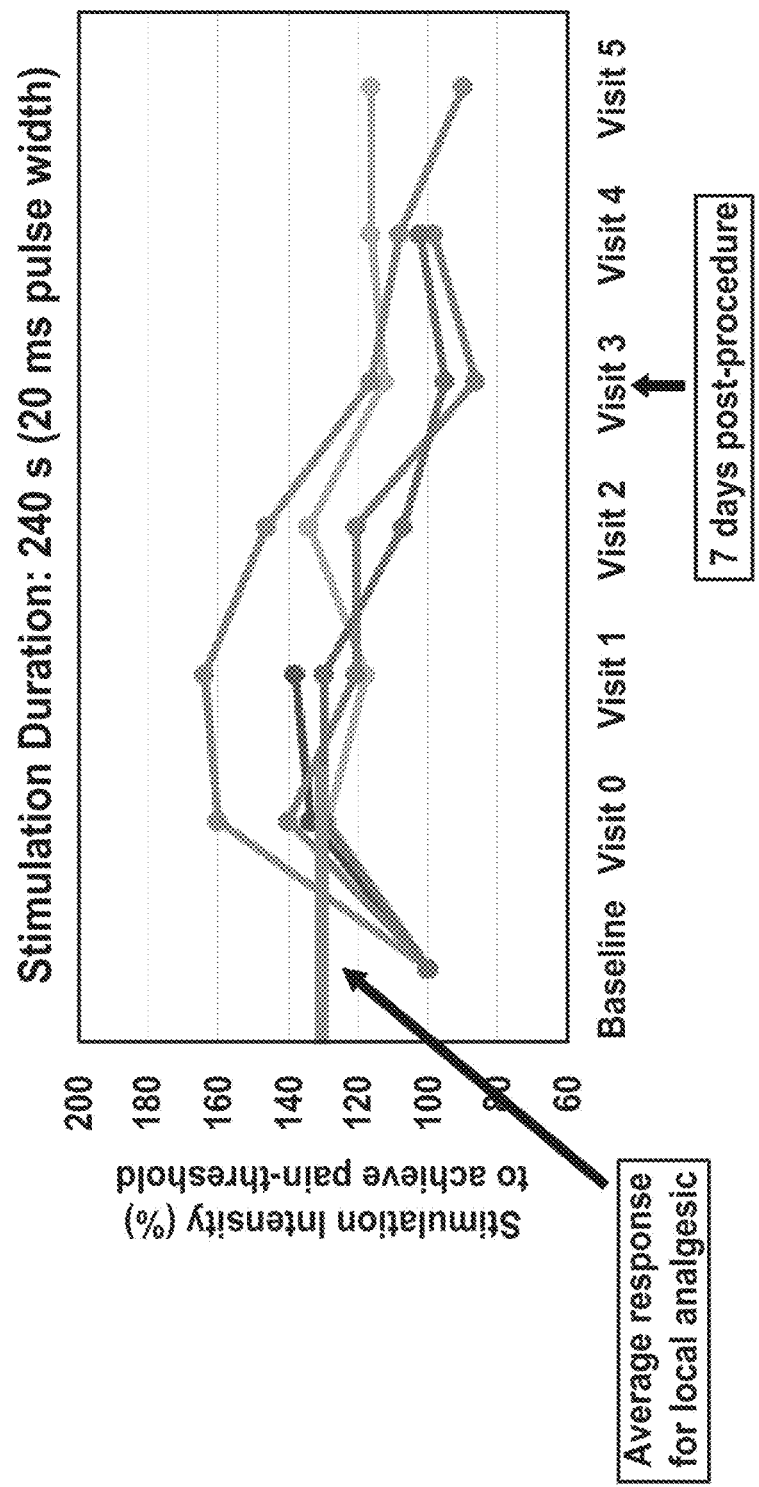
FIG. 7 is a table proving experimental results.

FIG. 7 shows the normalized pain thresholds over time for five subjects which received 240-s-duration electrical stimulation treatments. The green line shows the average response for local analgesics such as lidocaine or bupivacaine, which provide analgesia for a period of less than a day. An increase in pain thresholds was evident for all subjects, indicating a decreased sensitivity to pain. Return to baseline was evident by seven days post-procedure.

Figure 8:
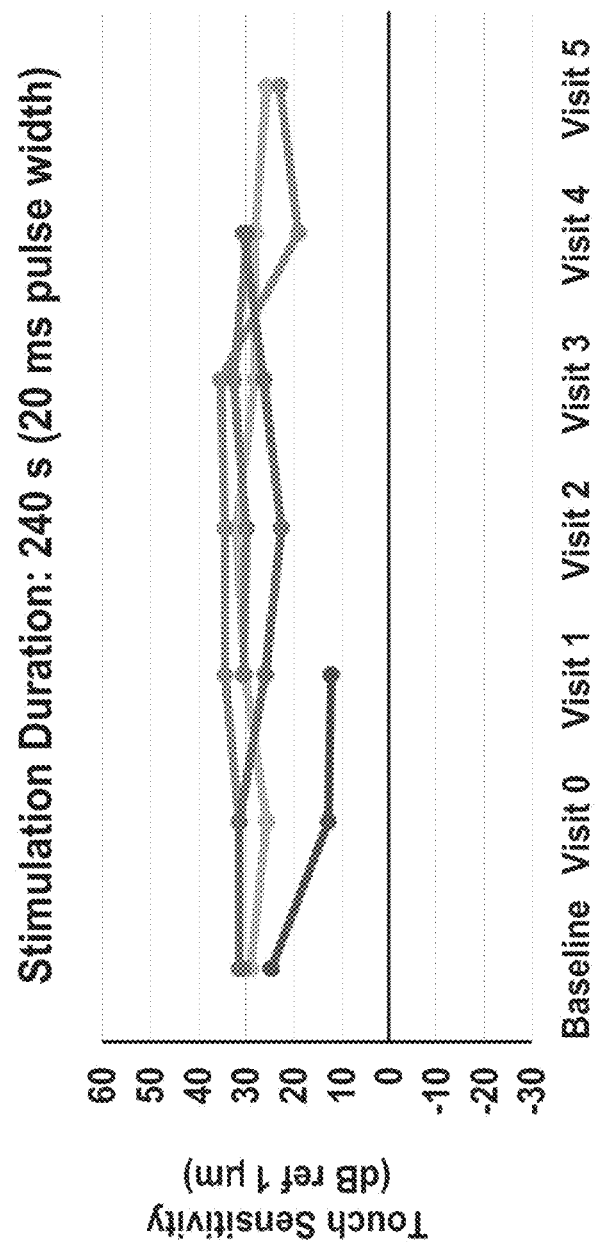
FIG. 8 is a table proving experimental results.

FIG. 8 shows the mechanical vibration thresholds over time for the same five subjects (240-s-duration electrical stimulation treatments). No systematic change in mechanical vibration thresholds was evident, suggesting selectivity of the treatment toward pain perception. Additionally, results of a clinical exam also did not indicate any sensory deficits on the treated leg.

These results suggest that the electrical stimulation treatment selectively and reversibly increases the threshold to perception of pain via a treated nerve with full reversibility within 7 days after treatment.

Example Computing System

While the methods and systems have been described in connection with preferred embodiments and specific examples, it is not intended that the scope be limited to the particular embodiments set forth, as the embodiments herein are intended in all respects to be illustrative rather than restrictive.

As used herein, "computing device" may include a plurality of computers. The computers may include one or more hardware components such as, for example, a processor, a random access memory (RAM) module, a read-only memory (ROM) module, a storage, a database, one or more input/output (I/O) devices, and an interface. Alternatively, and/or additionally, controller may include one or more software components such as, for example, a computer-readable medium including computer executable instructions for performing a method associated with the exemplary embodiments. It is contemplated that one or more of the hardware components listed above may be implemented using software. For example, storage may include a software partition associated with one or more other hardware components. It is understood that the components listed above are exemplary only and not intended to be limiting.

Processor may include one or more processors, each configured to execute instructions and process data to perform one or more functions associated with a computer for indexing images. Processor may be communicatively coupled to RAM, ROM, storage, database, I/O devices, and interface. Processor may be configured to execute sequences of computer program instructions to perform various processes. The computer program instructions may be loaded into RAM for execution by processor. As used herein, processor refers to a physical hardware device that executes encoded instructions for performing functions on inputs and creating outputs.

A processor can be microcontrollers, microprocessors, or logic circuits such as ASICs (Application Specific Integrated Circuit), CPLDs (Complex Programmable Logic Device), FPGA (Field Programmable Gate Array), or other programmable logic integrated circuits. In some embodiments, a processor is configured to execute instruction stored in a memory of the device.

RAM and ROM may each include one or more devices for storing information associated with operation of processor. For example, ROM may include a memory device configured to access and store information associated with controller, including information for identifying, initializing, and monitoring the operation of one or more components and subsystems. RAM may include a memory device for storing data associated with one or more operations of processor. For example, ROM may load instructions into RAM for execution by processor.

Storage may include any type of mass storage device configured to store information that processor may need to perform processes consistent with the disclosed embodiments. For example, storage may include one or more magnetic and/or optical disk devices, such as hard drives, CD-ROMs, DVD-ROMs, or any other type of mass media device.

Database may include one or more software and/or hardware components that cooperate to store, organize, sort, filter, and/or arrange data used by controller and/or processor 122. For example, database may store hardware and/or software configuration data associated with input-output hardware devices and controllers, as described herein. It is contemplated that database may store additional and/or different information than that listed above.

I/O devices may include one or more components configured to communicate information with a user associated with controller. For example, I/O devices may include a console with an integrated keyboard and mouse to allow a user to maintain a database of images, update associations, and access digital content. I/O devices may also include a display including a graphical user interface (GUI) for outputting information on a monitor. I/O devices may also include peripheral devices such as, for example, a printer for printing information associated with controller, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface may include one or more components configured to transmit and receive data via a communication network, such as the Internet, a local area network, a workstation peer-to-peer network, a direct link network, a wireless network, or any other suitable communication platform. For example, interface may include one or more modulators, demodulators, multiplexers, demultiplexers, network communication devices, wireless devices, antennas, modems, and any other type of device configured to enable data communication via a communication network.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed:

1. A system for modulating targeted neural and non-neural tissue of a nervous system structure to treat a medical condition of a patient, the system comprising:
    an electrical stimulation device comprising an elongated body sized and configured to be advanced through a body orifice, the elongated body comprising an electrode provided at a distal end of the elongated body, the electrode sized and configured to be placed in contact with a mucosal tissue of the patient, the electrode is configured to deliver a transmucosal electrical stimulation to a treatment site proximate the targeted neural and non-neural tissue of the nervous system structure underlying the mucosal tissue; and
    a controller configured to connect to the electrode of the electrical stimulation device and to a power source configured to supply electrical energy to the electrode, wherein the controller is configured to direct operation of the electrical stimulation device to apply the transmucosal electrical stimulation to the treatment site through the electrode,
    wherein the controller is configured to direct operation of the electrical stimulation device to apply the transmucosal electrical stimulation to the treatment site to selectively modulate the targeted neural and non-neural tissue of the nervous system structure to reversibly inhibit the perception of pain and preserve other sensory and motor function, and proprioception,
    wherein the controller is configured to direct operation of the electrical stimulation device to apply the transmucosal electrical stimulation to the treatment site as a pulse duty cycle selected to not damage the mucosal tissue and to not damage the targeted neural and non-neural tissue.

2. The system of claim 1, wherein the pain comprises at least one of head-and-face pain, a migraine headache, a cluster headache, an occipital neuralgia, a tension headache, a sinus headache, cervicogenic headache, postherpetic neuralgia, post-traumatic pain, or chronic daily headache,
    wherein the controller directs operation of the electrical stimulation device to administer a single application of the transmucosal electrical stimulation to the treatment site to selectively modulate the targeted neural and non-neural tissue and to result in subsequent inhibition of perception of pain, for a period of 1 day to 30 days.

3. The system of claim 1, wherein the electrode is sized and configured to be placed in contact with mucosal tissue comprising at least one of an oral mucosa, a nasal oral mucosa, a gastrointestinal (GI) tract mucosa, a bowel mucosa, or a bladder mucosa.

4. The system of claim 1, wherein the electrode is configured to deliver electrical stimulation to the treatment site proximate targeted neural and non-neural tissue of at least one of a sphenopalatine ganglion or a gasserian ganglion.

5. The system of claim 1, wherein the controller is configured to direct operation of the electrical stimulation device to apply electrical stimulation to the treatment site to modulate the targeted neural and non-neural tissue thereby inhibiting nerve signal transmission through nerve fibers that are responsible for the transmission of pain, while nerve signal transmission through nerve fibers responsible for other sensory and motor function, and proprioception is preserved,
    wherein other sensory function includes at least one of touch, vision, audition, gustation, olfaction, or balance.

6. The system of claim 1, wherein the nervous system structure comprises the sphenopalatine ganglion (SPG),
wherein the electrode is sized and configured to be positioned adjacent in contact with the mucosal tissue overlying the SPG such that the electrode has at least one of a size-, shape-, or contact-surface configuration suitable to deliver the transmucosal electrical stimulation to the SPG and surrounding non-neural tissue,
wherein the transmucosal electrical stimulation selectively inhibits nerve signal transmission through at least one of a select type of nerve fiber of the SPG, wherein function of at least one of a non-selected nerve fiber is selectively preserved.

7. The system of claim 6, wherein the transmucosal electrical stimulation delivered to the target site differentially inhibits the function of the select type of nerve fiber of the SPG,
wherein the select type of nerve fiber of the SPG has a larger percentage of fibers inhibited than the non-selected type of fiber of the SPG and the non-neural tissue.

8. The system of claim 1, wherein the nervous system structure comprises the sphenopalatine ganglion (SPG),
wherein the controller is adjustable to vary a parameter of the transmucosal electrical stimulation delivered to the treatment site to selectively modulate the neural and non-neural tissue of the SPG and selectively modulate nerve signal transmission through nerve fibers of the SPG responsible for the transmission of pain,
wherein the parameter is selected from the group consisting of a waveform shape, a waveform frequency, a waveform amplitude, an electrical field strength generated at the electrode, a waveform DC offset, and a waveform duty cycle, a tissue temperature, an electrode temperature, a cooling mechanism parameter, and a treatment duration.

9. The system of claim 8, wherein the transmucosal electrical stimulation delivered to the target site for modulating function of the SPG has a frequency ranging from 100 kHz to 1 MHz, intensity ≤1,000 mA and ≤1,000 V, and an electrical field strength ≤1,000,000 V/m.

10. The system of claim 1, the transmucosal electrical stimulation delivered to the treatment site has at least one of:
a pulsed waveform with an envelope ≤1000 ms, an envelope delivery frequency ≤100 Hz, and for durations ≤30 minutes,
a frequency selected from the group consisting of 100 kHz, 200 kHz, 300 kHz, 400 kHz, 500 kHz, 600 kHz, 700 kHz, 800 kHz, 900 kHz and 1 MHz,
an amplitude ranging from 10 mA to 5,000 mA,
an amplitude ranging from 10 V to 1,000 V,
a power ranging from 1 W to 1,250 W,
a generated or induced electrical field strength at the target site and/or the electrode ranging from 20 V/m to 1,000,000 V/m,
a waveform shape component including at least one of a sinusoidal waveform, a square waveform, a triangular waveform, an impulse waveform, a shape modulated waveform, a frequency modulated waveform, or an amplitude modulated waveform that provides a continuous delivery of electrical stimulation at the treatment site and a combination thereof,
a duty cycle ranging from 0.1% to 99%,
an inter-pulse width ranging from 1 ms to 999 ms, or
a duration up to 30 minutes.

11. The system of claim 1, wherein the controller is adjustable to apply the transmucosal electrical stimulation while maintaining a tissue temperature and/or a temperature of the electrode ranging from 5° C. to 60° C.

12. The system of claim 1, wherein the electrode is sized and shaped to maximize and direct the electrical field toward the nervous system structure,
wherein the nervous system structure comprises at least one of a sphenopalatine ganglion or a gasserian ganglion,
wherein an electrical contact of the electrode has a surface area ranging between 1 mm$^2$ to 100 mm$^2$,
wherein a shape of the electrode comprises at least one of an elongated triangular shape, a ball-tipped shape, a half-ball shape, or flat circular shape.

13. The system of claim 1, wherein the elongated body is sized and configured to be advanced through the nostril of the patient and along the middle nasal turbinate,
wherein the electrode has a contact surface having a size and shape corresponding to a size and shape of a sphenopalatine ganglion (SPG), such that the energy provided at the electrode can modulate the entire SPG simultaneously and the electrode can provide a uniform pressure on a mucosal layer proximate the SPG.

14. The system of claim 13, wherein the elongated body portion extends between a proximal and the distal end of the stimulation,
wherein the proximal end of the stimulation device extends through the nostril of the patient when the electrode is position in contact with the mucosal tissue overlying SPG,
wherein a length of the elongated body portion ranges between 5 cm and 20 cm,
wherein a contact surface area of the electrode ranges between 1.57 mm$^2$ and 56 mm$^2$.

15. The system of claim 14, wherein the elongated body portion includes a contour corresponding to a superior border of the middle nasal turbinate of a patient,
wherein the elongated body portion is constructed from a flexible material suitable for insertion through the nasal cavity of the patient.

16. The system of claim 1, wherein the controller is adjustable to vary the transmucosal electrical stimulation based on a measured feedback selected from the group consisting of: a measured inhibition of nerve signal transmission; a measured temperature of at least one of the treatment site, the electrodes or a portion thereof, the electrical stimulation device, or the patient's skin; input from the patient; a feedback corresponding to at least one of the adjustable parameters; a treatment setting associated with a time course of recovery; electrode contact impedance; electric field generated in the tissue; patient physiological response including at least one of blood flow, skin conductance, heart rate, or muscle activity.

17. The system of claim 1, further comprising:
a temperature sensor coupled to the stimulation device for measuring a temperature of at least one of i) a contact surface of the stimulation device or ii) the patient's tissue in contact with the contact surface or electrode, where the temperature sensor is coupled to the controller and provides thermal feedback information regarding a measured temperature, and
a cooling mechanism configured to provide a cooling effect at the treatment site,
wherein the controller is adjustable to vary at least one parameter of the transmucosal electrical stimulation in response to the thermal feedback information from the temperature sensor to adjust a temperature of the contact surface below a destructive tissue temperature, wherein the controller is adjustable to vary operation of the cooling mechanism to provide the cooling effect at the treatment site to prevent damage at the treatment site in contact with the contact surface of the electrode.

18. The system of claim 1, further comprising:

at least one of a temperature sensor coupled to an outer surface of the patient's skin, a blood flow meter for coupling to the outer surface of the patient's skin, a skin conductance meter coupled to the outer surface of the patient's skin, or a heart rate monitor for measuring the patient's heart rate, wherein the controller is adjustable to vary at least one parameter of the transmucosal electrical stimulation in response to feedback information received from at least one of the temperature sensor, the blood flow meter, the skin conductance meter, or the heart rate monitor, wherein the at least one adjustable parameter is selected from the group consisting of a waveform shape, a waveform frequency, a waveform amplitude, an electrical field strength generated at the electrode, a waveform DC offset, a waveform duty cycle, a tissue temperature, and a cooling mechanism parameter.

* * * * *

UNITED STATES PATENT AND TRADEMARK OFFICE
CERTIFICATE OF CORRECTION

| | |
|---|---|
| PATENT NO. | : 11,504,534 B2 |
| APPLICATION NO. | : 16/705904 |
| DATED | : November 22, 2022 |
| INVENTOR(S) | : Eric A. Schepis et al. |

It is certified that error appears in the above-identified patent and that said Letters Patent is hereby corrected as shown below:

In the Claims

Column 47, Lines 3-4 Claim 6 delete, "...to be positioned adjacent in contact with..." and insert, --to be positioned in contact with--

Signed and Sealed this
Twenty-first Day of March, 2023

*Katherine Kelly Vidal*

Katherine Kelly Vidal
*Director of the United States Patent and Trademark Office*